US007282593B2

(12) United States Patent
Nair et al.

(10) Patent No.: US 7,282,593 B2
(45) Date of Patent: Oct. 16, 2007

(54) WITHANAMIDE AND WITHANOLIDE COMPOSITIONS AND METHOD OF USE THEREOF

(75) Inventors: Muraleedharan G. Nair, Okemos, MI (US); Bolleddula Jayaprakasam, East Lansing, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 564 days.

(21) Appl. No.: 10/918,284

(22) Filed: Aug. 13, 2004

(65) Prior Publication Data

US 2005/0059727 A1 Mar. 17, 2005

Related U.S. Application Data

(60) Provisional application No. 60/501,985, filed on Sep. 11, 2003.

(51) Int. Cl.
*C07D 405/00* (2006.01)
(52) U.S. Cl. ...................................... 548/454
(58) Field of Classification Search ................. 548/454
See application file for complete search history.

(56) References Cited

FOREIGN PATENT DOCUMENTS

WO WO98-48788 A1 11/1998

OTHER PUBLICATIONS

Thakur, R.S., et al., Major medicinal plants of India; Ed.; Central Institute of Medicinal and Aromatic Plants: Lucknow, India, 531 (1989).
Ray, A. B., et al., Prog. Chem. Org. Nat. Prod. 63, 1-106 (1994).
Matsuda, M., et al., Bioorg. Med. Chem. 9, 1499-1507 (2001).
Stoller E.W., et al., Lloydia, 37, 309-312 (1974).
Anjaneyulu,A. S. R., et al., Studies in Natural Products Chemistry:Structure and Chemistry (Part F); Ed. Atta-ur-Rahman, vol. 20, 135-261 (1998).
Newman, D.J., et al., J. Nat. Prod. 66 1022-1037 (2003).
Misico, R.I., et al., J. Nat. Prod. 65, 677-680 (2002).
Su, B. N., et al., Tetrahedron 58, 3453-3466 (2002).
Wickens, A.P., Respiration Physiology, 128 371-3891 (2001).
Vaya, J., et al., Curr. Med. Chem. Imm., Endoc. & Metab. Agents 1 99-117 (2001).
West, I.C., Diabet Med. 17 171-180 (2000).
Temple, N.J., Nutr. Res. 20 449-459 and references cited therein (2000).
Conclin, K.A., Nut. Canc. 37 1-18 (2000).
Marchant, C.A., Env. Health Persp. Supp. 104 1065-1073 (1996).
Spinell, A., et al., J. Org. Chem. 62 5471-5475 (1997).
Jayaprakasam, B., et al., Tetrahedron 59 841-849 (2003).
Reznaka, T., et al., Phytochemistry 54 635-645 (2000).
Arora, A., et al., Free Radical Biology & Medicine 24 1355-1363 (1998).
Tian, Q., et al., Nutr. Cancer 40 180-184 (2001).
Linnoila, V., et al., J. Clin. Psychiatry 53 46-51 (1992).
Wurtman, J., J. Clin. Psychiatry 49 37-39 (1998).
Birdsall, T.C., Altern Med Rev. 3 271-280 and references cited therein (1998).

*Primary Examiner*—D. Margaret Seaman
*Assistant Examiner*—Nizal S. Chandrakumar
(74) *Attorney, Agent, or Firm*—Ian C. McLeod

(57) ABSTRACT

Novel isolated and purified withanamides and withanolides are described. In particular, compounds from *Withania somnifera* fruit are the preferred source of the withanamides and withanolides, although they can be from other plant sources. In addition to their use as powerful antioxidants, the withanamides and withanolides can be useful for the treatment of depression, Alzheimer's Disease, obesity and migraine headaches.

10 Claims, 5 Drawing Sheets

WITHANAMIDE AND WITHANOLIDE COMPOSITIONS AND METHOD OF USE THEREOF

CROSS-REFERENCE TO RELATED APPLICATIONS

This application claims the benefit of U.S. Provisional Application: 60,501,985 filed on Sep. 11, 2003.

BACKGROUND OF THE INVENTION (1) Field of the Invention

The present invention relates to the use of isolated and purified withanamides and withanolides in the treatment of various diseases, such as Alzheimer's Disease, depression, obesity and migraine headaches. The withanamides and withanolides were particularly isolated and purified from fruits of *Withania somnifera*.

(2) Description of Related Art

*Withania somnifera* (L) Dunal of solanaceae, is an erect evergreen shrub distributed throughout the drier parts of India. *W. somnifera*, known as Aswagandha, is well known for its use in Ayurvedic medicine. The Aswagandha root extract was reported as a folk remedy for adenopathy, arthritis, asthma, hypertension, inflammations, and rheumatism (Thakur, R. S., et al., *Major medicinal plants of India*; Ed.; Central Institute of Medicinal and Aromatic Plants: Lucknow, India, 531 (1989)). The leaves of *W. somnifera* were also used as a cure for several illnesses including tumors, inflammations, conjunctivitis and tuberculosis (Thakur, R. S., et al., *Major medicinal plants of India*; Ed.; Central Institute of Medicinal and Aromatic Plants: Lucknow, India, 531 (1989)). Currently, powdered roots or root extract of this plant are used as a dietary supplement in the United States.

The major chemical constituents reported from *W. somnifera* are called withanolides. These compounds are structurally diverse steroidal compounds with an ergosterol skeleton in which C-22 and C-26 are oxidized to form a δ-lactone; (Ray, A. B., et al., *Prog. Chem. Org. Nat. Prod.* 63, 1-106 (1994)). The chemical investigations of the roots and leaves of *W. somnifera* resulted in the isolation and characterization of several withanolides (Matsuda, M., et al., *Bioorg. Med. Chem.* 9, 1499-1507 (2001)). The fruits of this plant are tiny orange berries and reported to contain saturated and unsaturated fatty acids (Stoller E. W., et al., *Lloydia*, 37, 309-312 (1974); Monika, P., et al., *Asian J. Chem.* 6, 442-444 (1994); and Monika, P., et al., *Sci. Phys. Sci.* 5, 81-83 (1993)). However, leaves and fruits are not fully investigated for biological activities. The withanolides are classified according to their structural skeleton (Ray, A. B., et al., *Prog. Chem. Org. Nat. Prod.* 63, 1-106 (1994)) and the structural variation is responsible for the wide array of pharmacological activities. Withanolides have been studied for their anti-inflammatory, antitumor, cytotoxic, immunomodulating activities and for the protection against $CCl_4$-induced hepatotoxicity (Ray, A. B., et al., *Prog. Chem. Org. Nat. Prod.* 63, 1-106 (1994); and Anjaneyulu, A. S. R., et al., *Studies in Natural Products Chemistry: Structure and Chemistry* (Part F); Ed. Atta-ur-Rahman, Vol. 20, 135-261 (1998)). They were also reported to induce phase-II enzymes in animal models, which is considered to be one of the mechanisms in cancer chemoprevention (Misico, R. I., et al., *J. Nat. Prod.* 65, 677-680 (2002); and Su, B. N., et al., *Tetrahedron* 58, 3453-3466 (2002)).

The life-supporting oxygen becomes toxic to most aerobic organisms when exposed to greater concentrations. Reasons for this toxicity are due to the formation of superoxide ($O_2^-$), hydrogen peroxide ($H_2O_2$); and hydroxyl (—OH.) radicals during the conversion of oxygen to water in the mitochondria. The free radicals generated from environmental contaminants and by exogenous factors such as drugs, toxins and stress cause oxidative damage to biological macromolecular structure and function (Wickens, A. P., *Respiration Physiology*, 128 371-3891 (2001)). This will then lead to the progression of many disease processes including atherosclerosis, cardiovascular diseases and cancer. Several studies linked to the aging process to the generation of reactive oxygen and nitrogen (Vaya, J., et al., *Curr. Med. Chem. Imm., Endoc. & Metab. Agents* 1 99-117 (2001)). The oxidative stress also damages the pancreatic β-cell's function and results in diabetes (West, I. C., Diabet Med. 17 171-180 (2000)). The singlet oxygen reacts with polyunsaturated fatty acids to form lipid peroxides which in turn decompose to initiate the formation of mutagens. Therefore, natural products or chemicals with potential to scavenge singlet species can reduce biological disorders that limit the progression of various aging related diseases. Many epidemiological studies shows that diets rich in antioxidants play a major role in the prevention of heart disease, cancer, diabetes, and Alzheimer's disease (Temple, N. J., *Nutr. Res.* 20 449-459 and references cited therein (2000)).

Some of the pharmaceuticals prescribed for depression or anxiety contain natural antioxidants. Mixtures of ascorbic acid, pyridoxine, carotene, vitamin E, Zn, nicotinamide, and Se were effectively used to treat depression or anxiety (Horrobin, D. F., PCT Int. Appl. WO98-48788, A1 1998 1105 (1998)). Natural antioxidants are used as food additives to inhibit lipid peroxidation and to maintain the nutritional qualities of food. It is also known that antioxidants decrease the side effects of chemotherapy during cancer treatment (Conclin, K. A., *Nut. Canc.* 37 1-18 (2000)). The synthetic antioxidants used to prevent the lipid peroxidation in food are butylated hydroxyanisole (BHA), butylated hydroxytoluene (BHT), propyl gallate (PG), and tert-butylhydroquinone (TBHQ). However, synthetic antioxidants are considered to be potential carcinogens (Marchant, C. A., *Env. Health Persp. Supp.* 104 1065-1073 (1996)) and hence there is considerable interest in developing safe and natural antioxidants.

OBJECTS

It is therefore an object of the present invention to provide compositions and a method for inhibiting diseases in mammals susceptible to withanamide and withanolide treatment. These and other objects will become increasingly apparent by reference to the following description and the drawings.

SUMMARY OF INVENTION

The present invention relates to an isolated and purified withanamide of the formula:

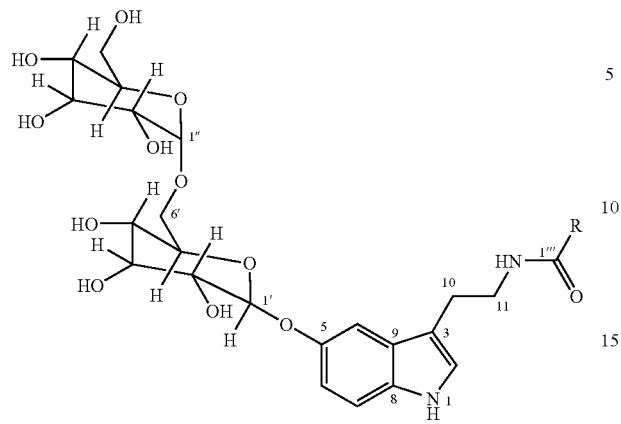
wherein R is selected from the group consisting of:
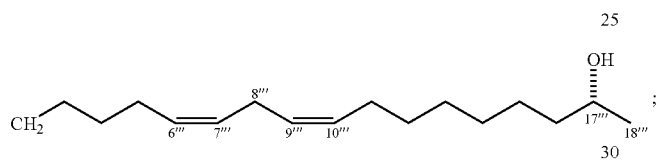
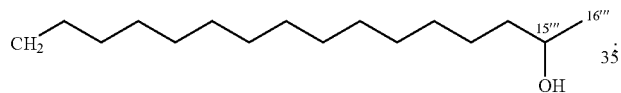
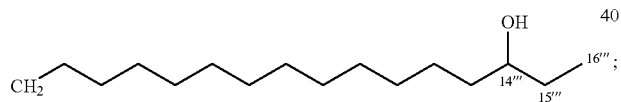
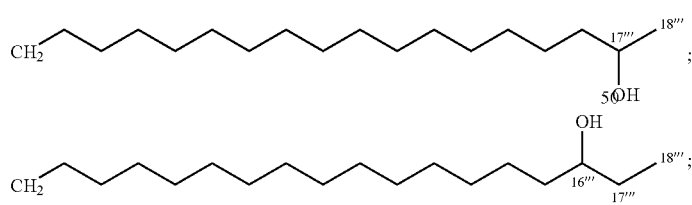
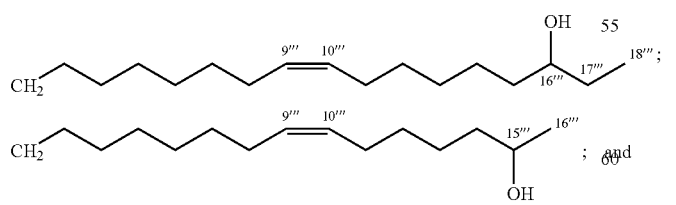
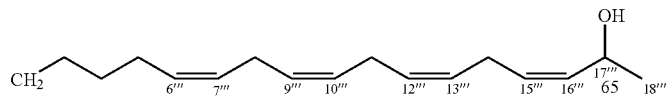

The present invention also relates to an isolated and purified compound of the formula
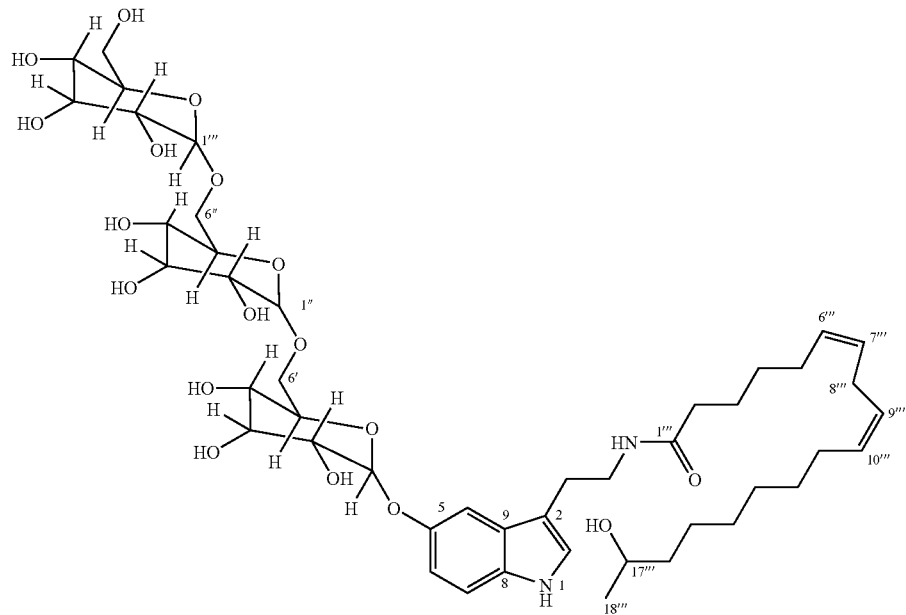
(9)
Further, the present invention relates to a method for treatment of a disease in vivo in a mammal which comprises:
administering an isolated and purified compound of the formula
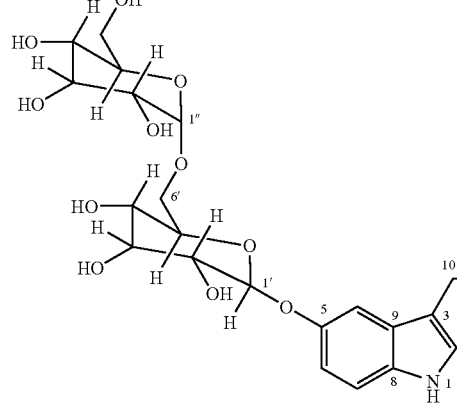
wherein R is selected from the group consisting of
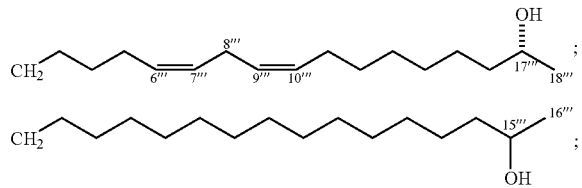
-continued
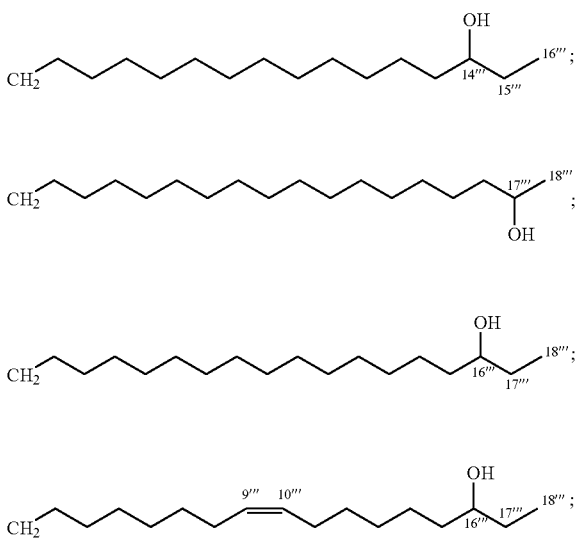
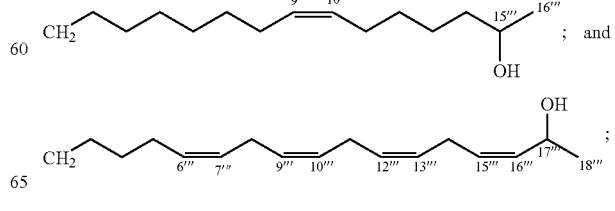

a compound of the formula
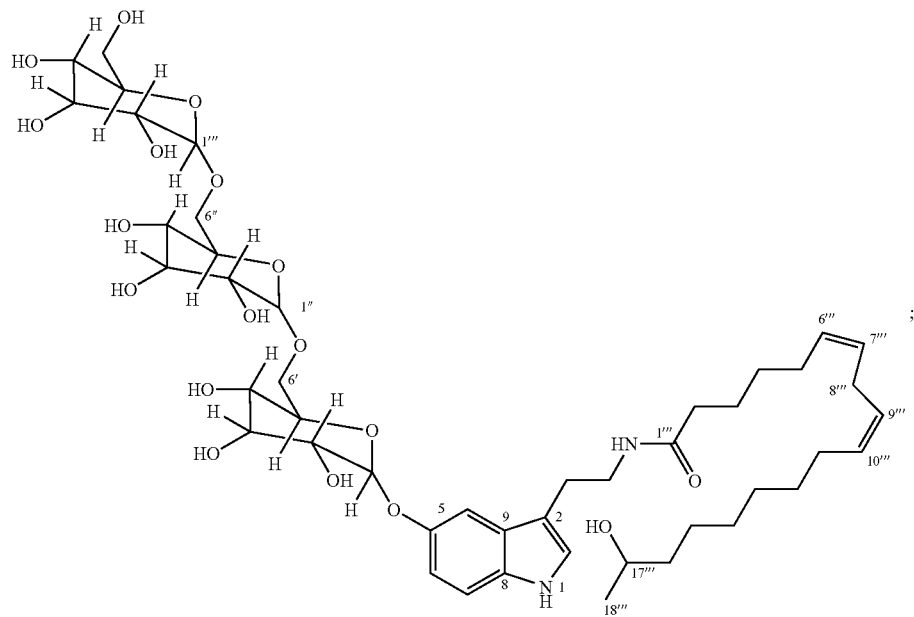
(9)
a compound of the formula:
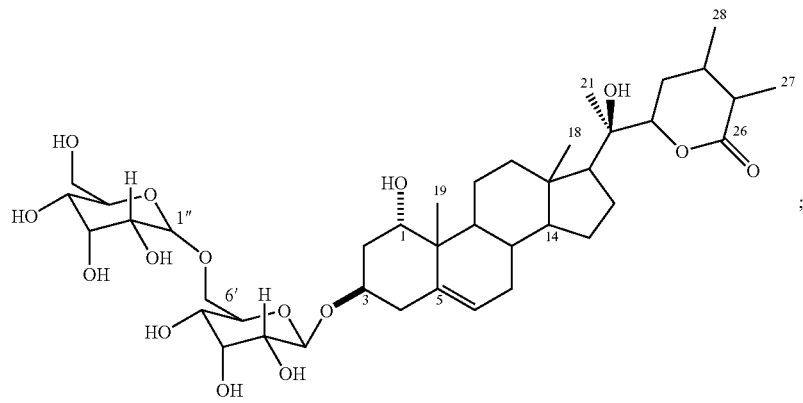
(10)

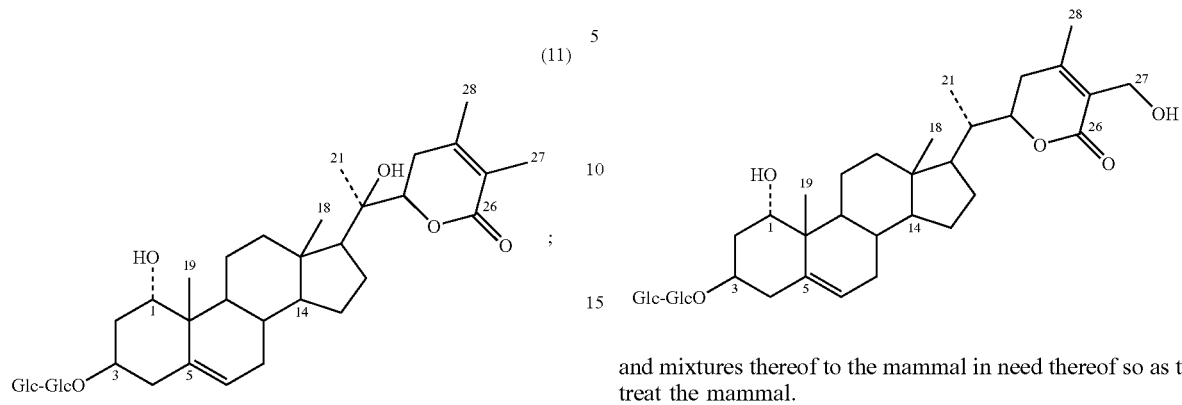

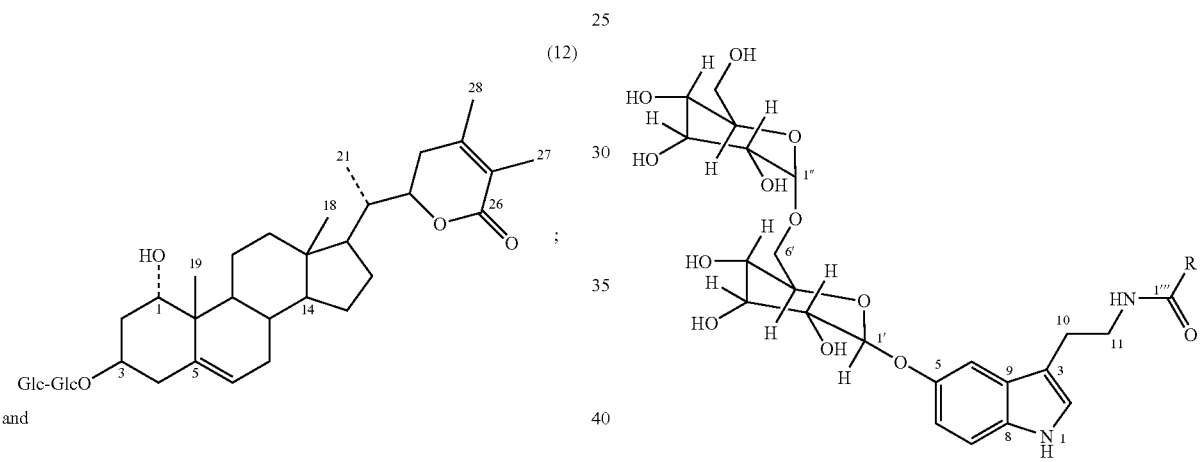

and mixtures thereof to the mammal in need thereof so as to treat the mammal.

The present invention further relates to a method for providing oxidation in a composition in need thereof which comprises introducing into the composition an effective amount of an isolated and purified compound selected from the group consisting of

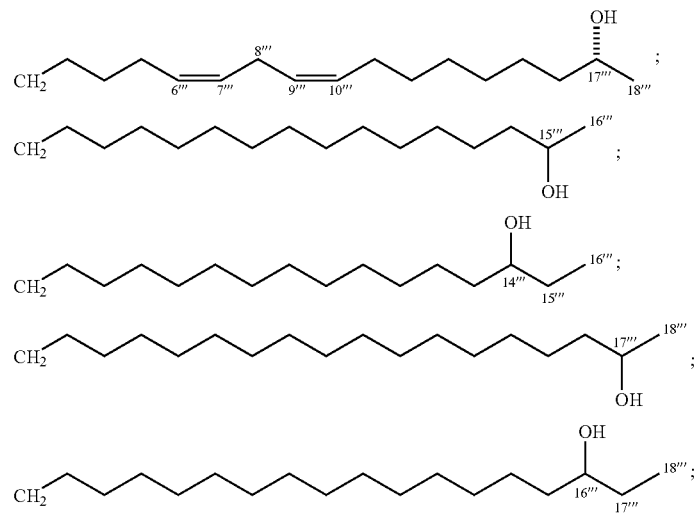

wherein R is selected from the group consisting of:

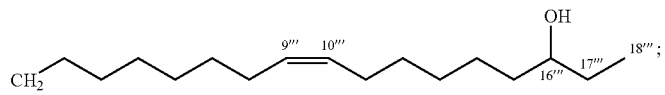
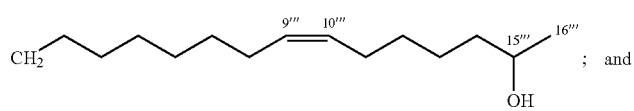; and
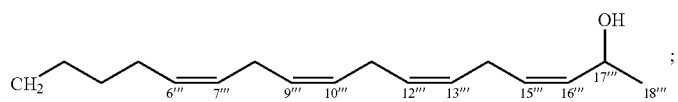
a compound of the formula
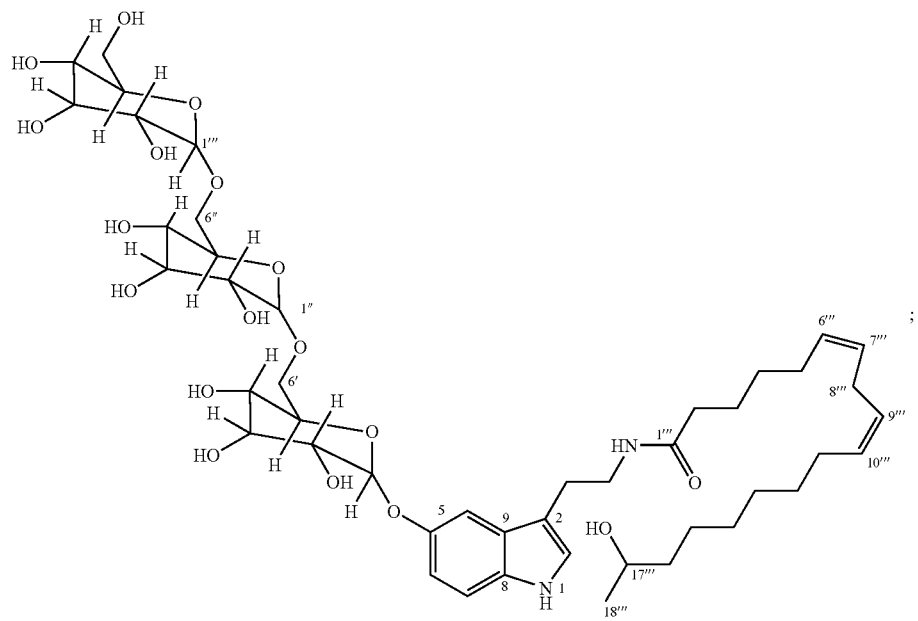
(9)

a compound of the formula
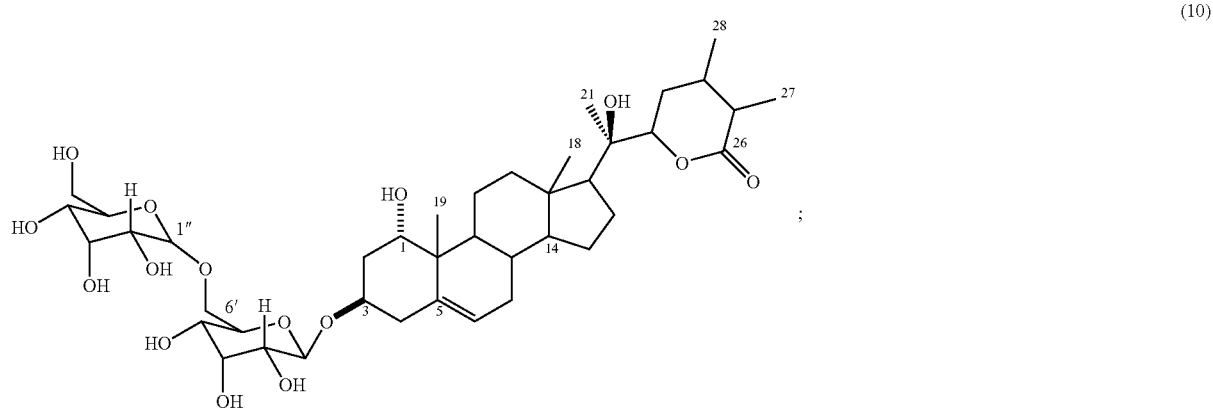
(10)
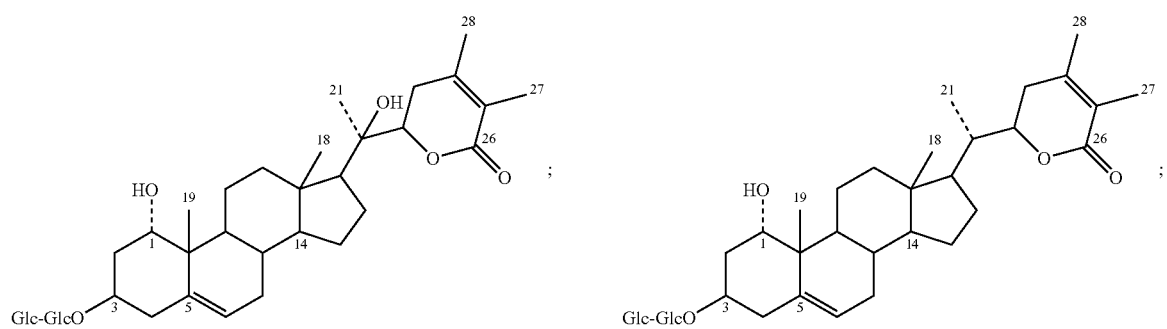
(11) (12)
and
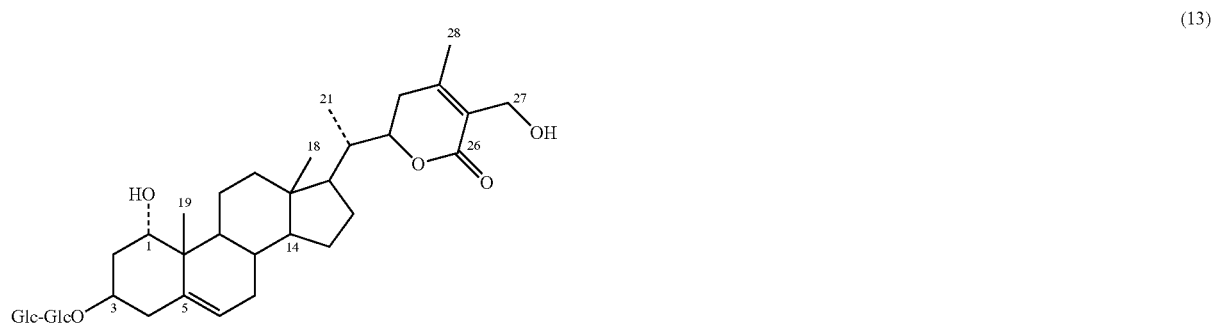
(13)
and mixtures thereof.

The present invention also relates to a composition which comprises:
(a) a composition in need of antioxidant activity; and
(b) an isolated and purified compound selected from the group consisting of
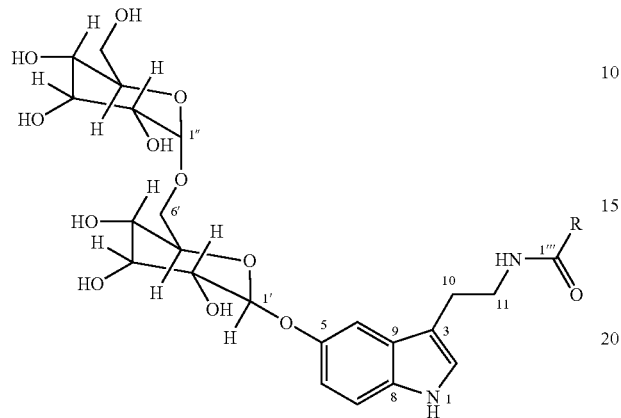
wherein R is selected from the group consisting of:
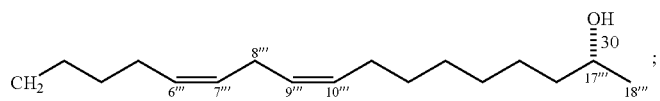
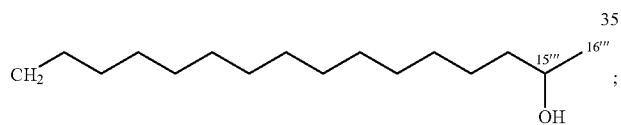
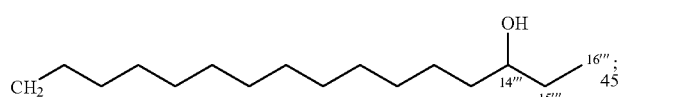
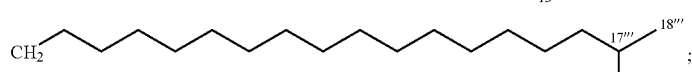
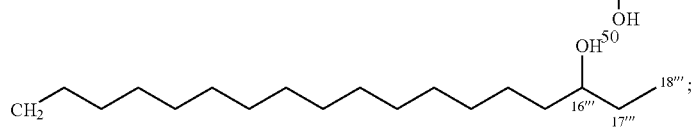
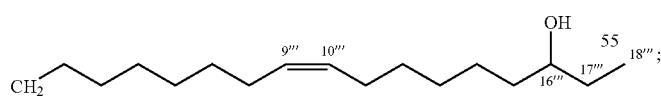
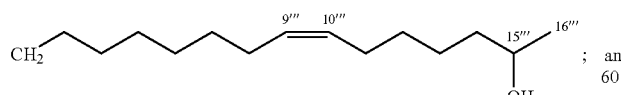; and
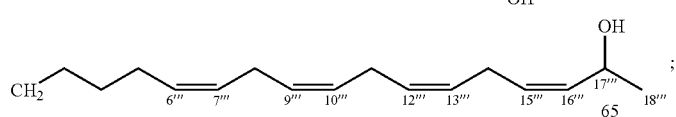;

a compound of the formula
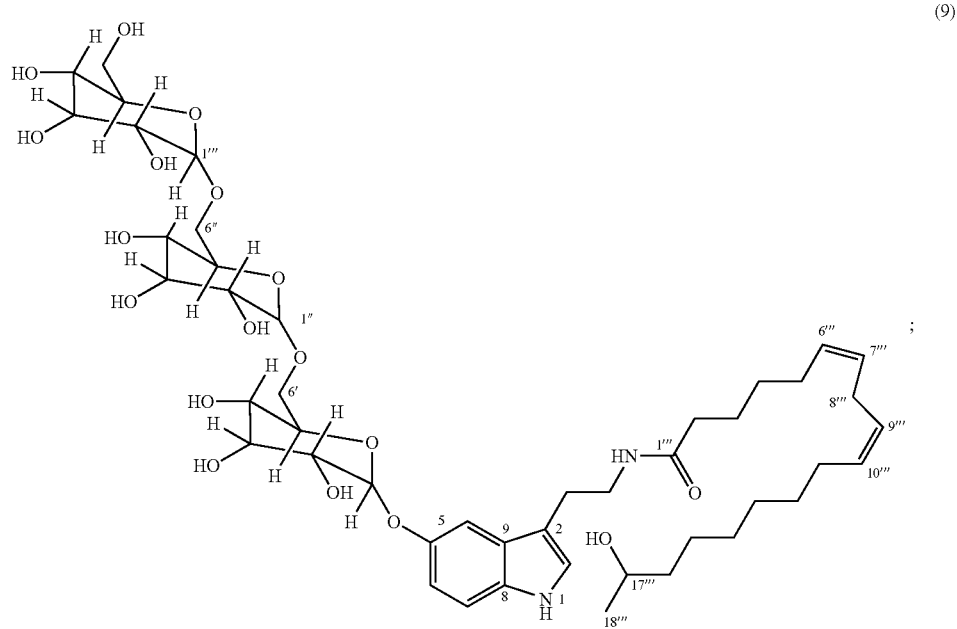
(9)
a compound of the formula:
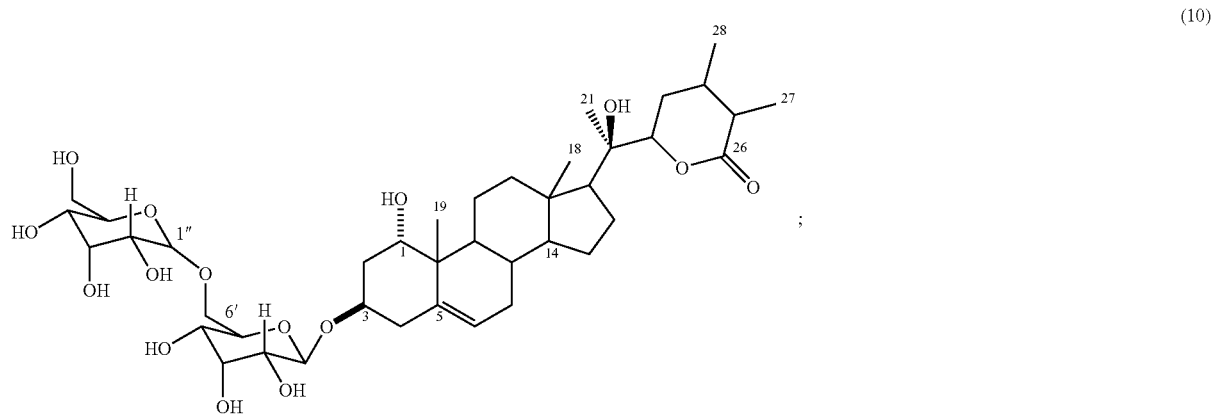
(10)

-continued
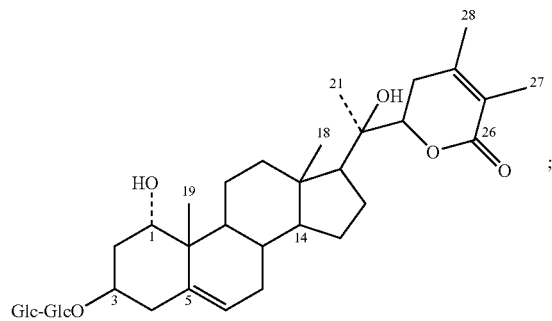
(11)
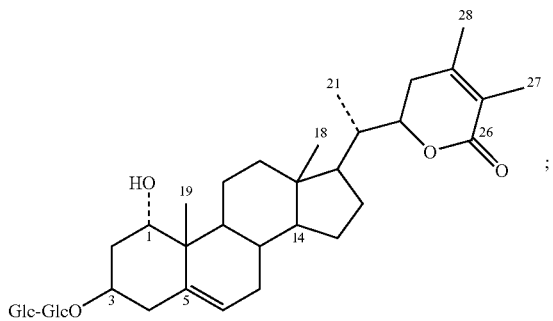
(12)
and
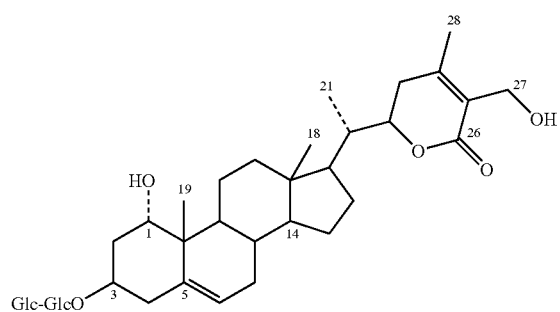
(13)

and mixtures thereof in an amount sufficient to provide the antioxidant activity.
The present invention also relates to a composition for use as a pharmaceutical which comprises:
(a) an isolated and purified compound selected from the group consisting of
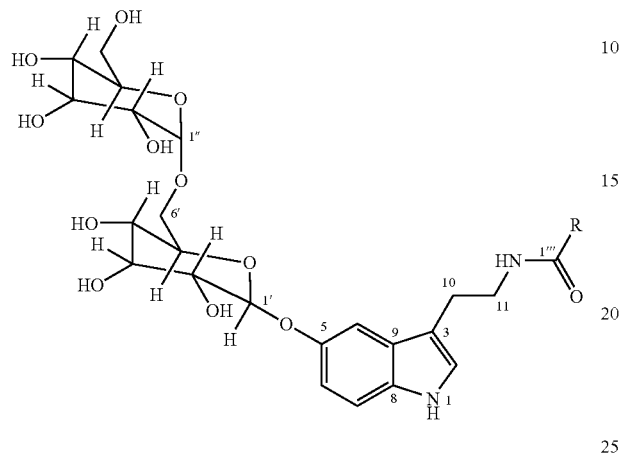
wherein R is selected from the group consisting of:
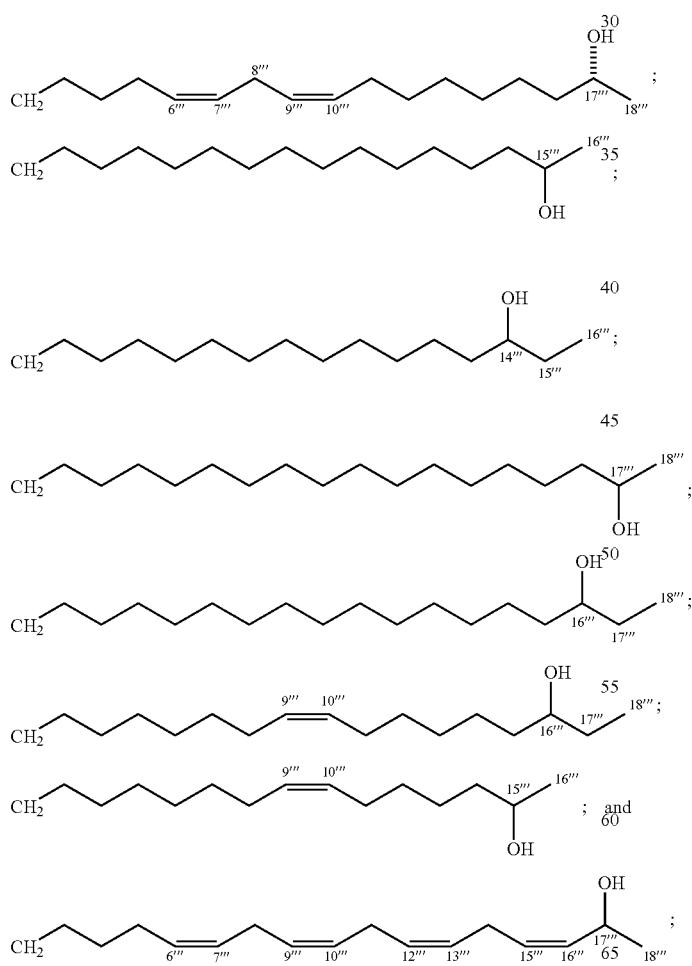

a compound of the formula
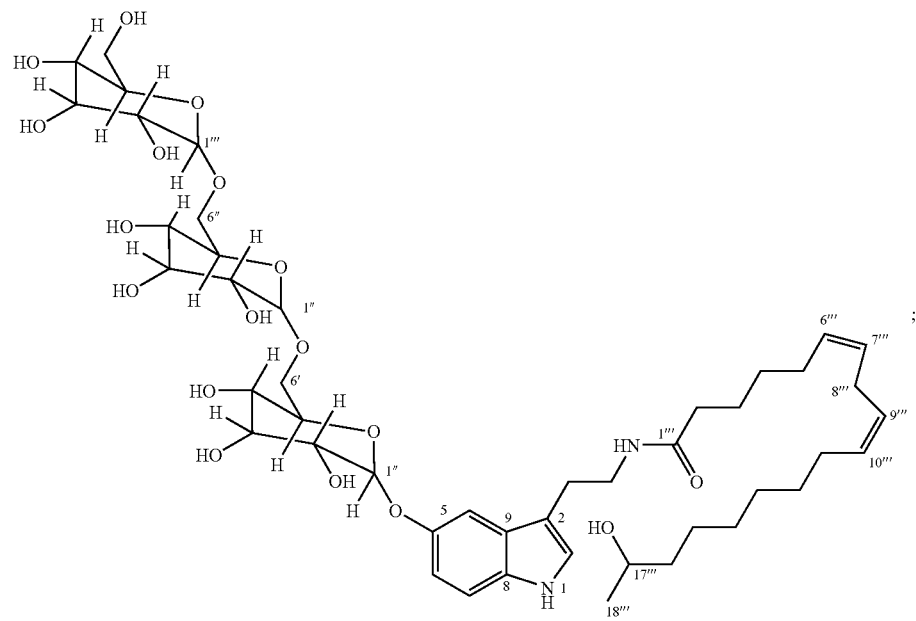
(9)
a compound of the formula
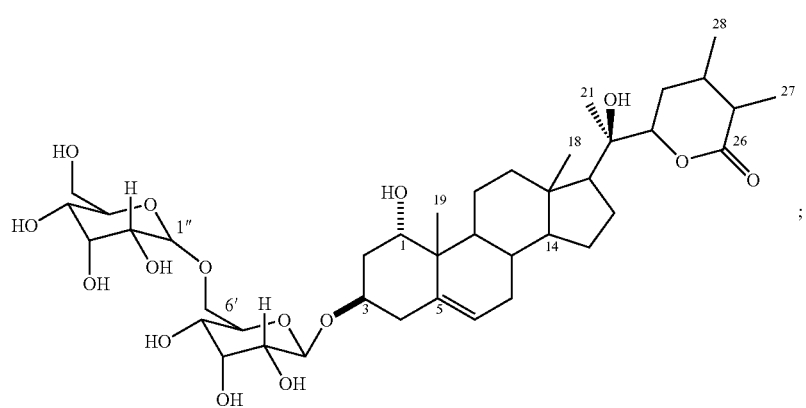
(10)

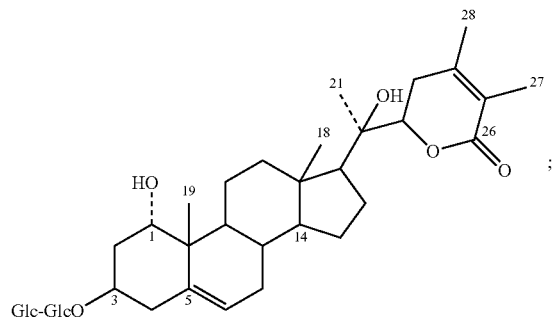 (11)

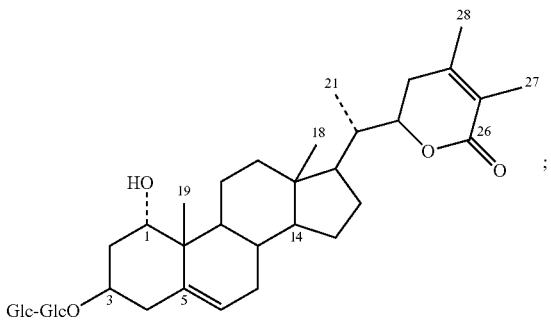 (12)

and

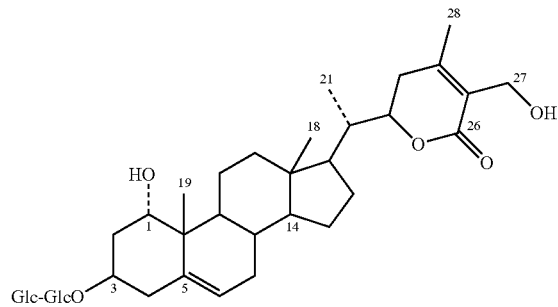 (13)

and mixtures thereof; and (b) a pharmaceutically acceptable carrier.

The present invention also relates to a method for treating a disease selected from the group consisting of Alzheimer's Disease, obesity, migraine headaches, and depression in a patient which comprises:

administering an effective amount of a composition comprising a withanamide, withanolide and mixtures thereof to the patient so as to relieve the depression.

The present invention also relates to a method for antioxidant treatment of a mammal in vivo which comprises:

administering an effective amount of a withanamide, withanolide and mixtures thereof to the mammal so as to provide antioxidant treatment of the mammal.

The present invention also relates to an isolated and purified withanolide of the formula:

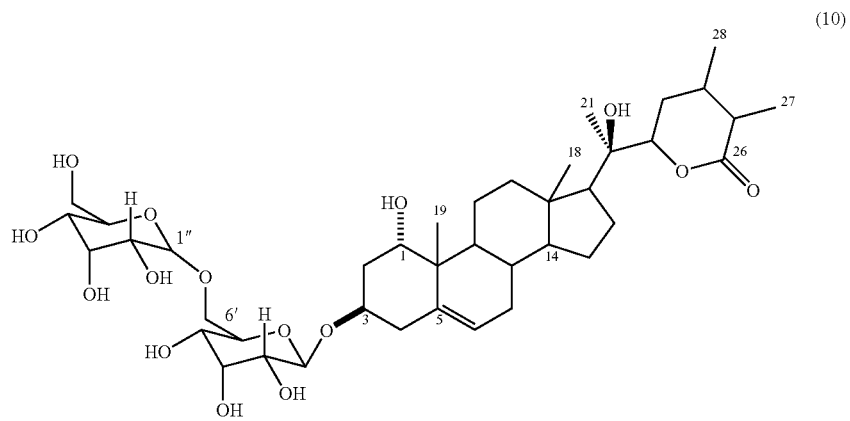
(10)

DESCRIPTION OF PREFERRED EMBODIMENTS

Figure 1:
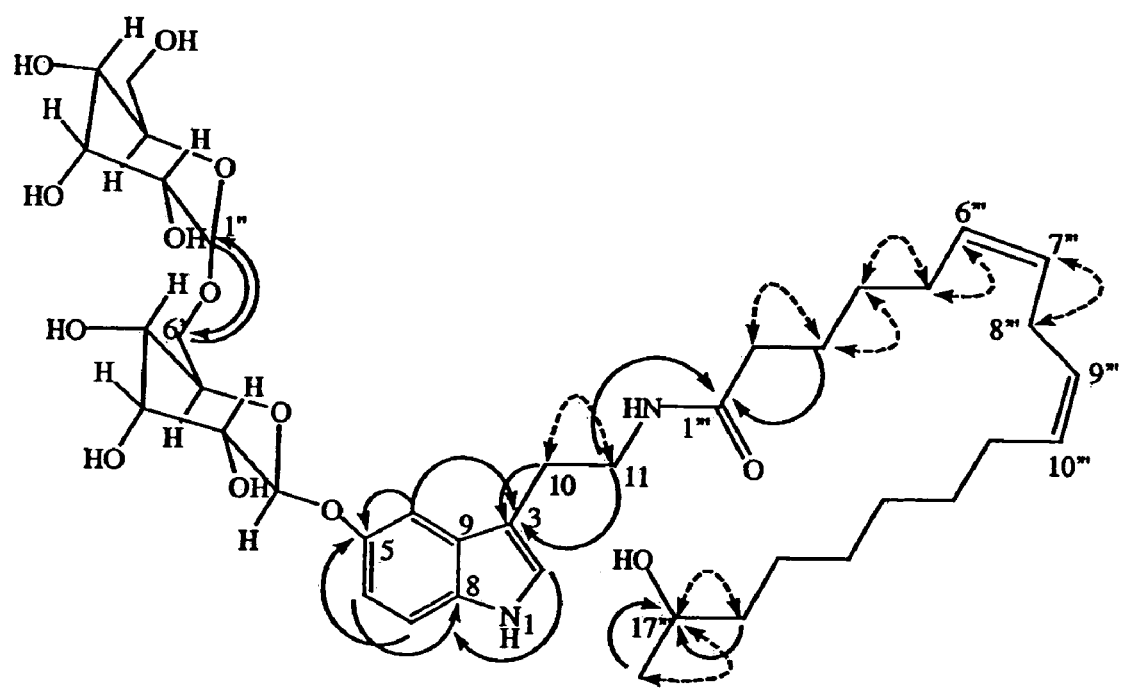
FIG. 1 is a chemical structure showing selected HMBC (→) and COSY (<-→) correlations observed in compound 1.

All patents, patent applications, government publications, government regulations, and literature references cited in this specification are hereby incorporated herein by reference in their entirety. In case of conflict, the present description, including definitions, will control.

It has been discovered that extracts of seeds of *W. somnifera* possess excellent lipid peroxidation inhibitory activity. The isolation and characterization of several novel withanamides and withanolides and a number of known withanolides from *W. somnifera* seed extracts is disclosed.

A bioassay-guided purification of the methanolic extract of *Withania somnifera* fruits yielded novel withanamides A-I (1-9), a new withanolide (10) and three known withanolides (11-13).

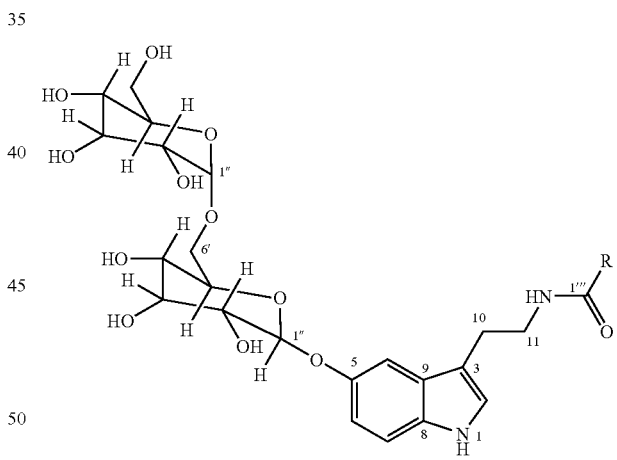

wherein R is selected from the group consisting of:

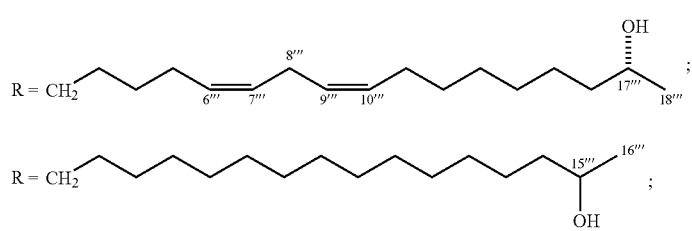

-continued
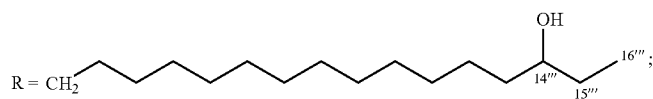
3
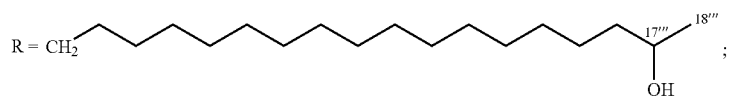
4
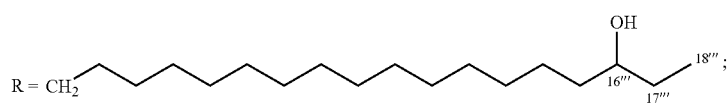
5
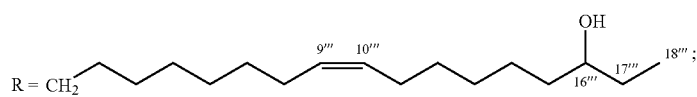
6
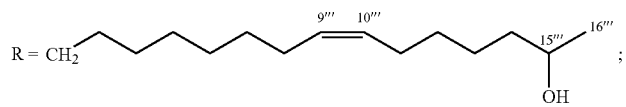
7
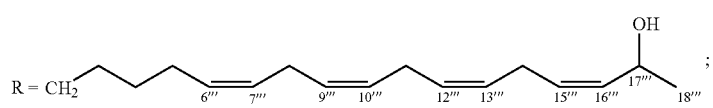
8
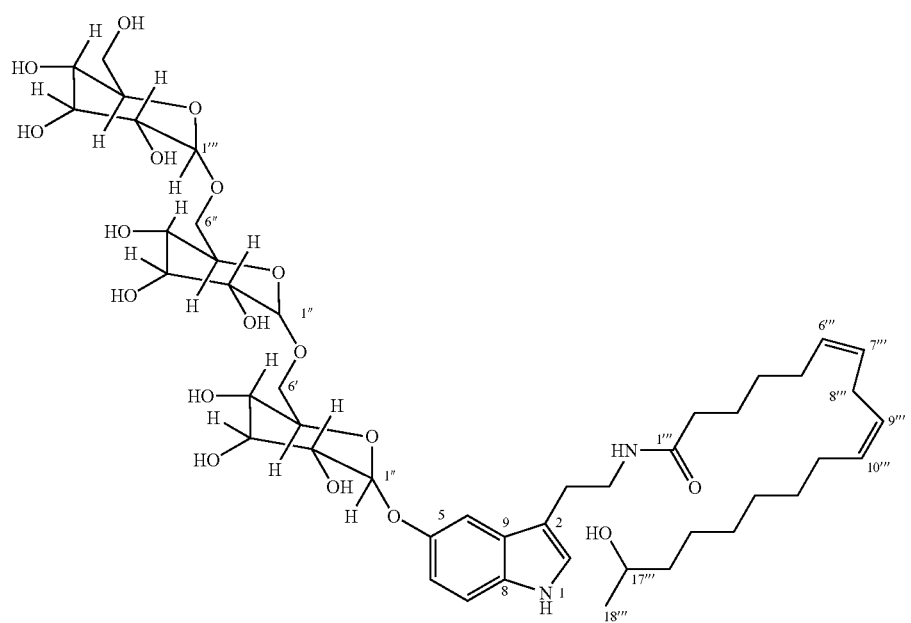
9

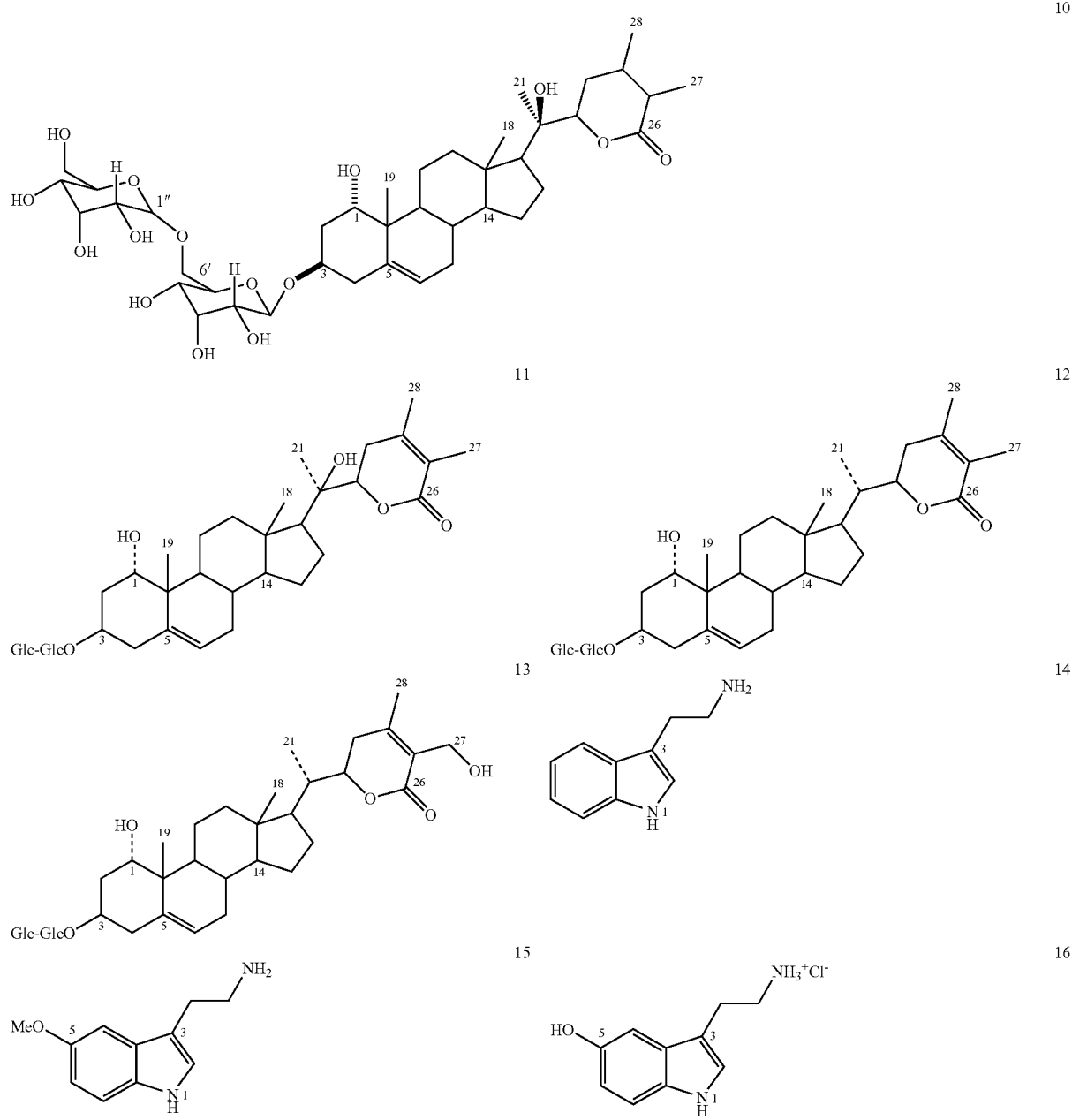

The structures of these compounds were determined by using FABMS, HRFABMS, ID- and 2D-NMR spectral experiments. The withanamides A-I (1-9) were found to be glycosylated serotonine conjugated with long-chain hydroxyl fatty acids. The stereochemistry of the hydroxyl group on the long-chain fatty acid moiety was determined by modified Mosher's ester method for compound 1. Compounds 1-13 were tested for their ability to inhibit lipid peroxidation in a model system using large unilamellar vesicles (LUV's). Withanamides 1-5 and 9 inhibited lipid peroxidation by 98, 93, 79, 94, 81 and 86%, respectively, at 1 μg/mL. However, compounds 6-8, inhibited the lipid peroxidation by 85, 82 and 90%, respectively at 0.5 μg/mL. Withanolides 10 and 13 were tested at 100 μg/mL and gave 84 and 25% of inhibition in this assay. Compounds 11 and 12 inhibited the lipid peroxidation by 86 and 82% at 50 and 10 μg/mL, respectively. To evaluate the structure activity relationships (SRA) of withanamides A-I, compounds 14-16 were purchased and determined their antioxidant activity using the same liposome model system. Commercial antioxidants butylated hydroxyanisole (BHA), butylated hydroxytoluene (BHT), and tert-butylhydroquinone (TBHQ), used as food preservatives, were also tested in this way at 1 μg/mL, respectively, and showed 80, 81 and 85% of inhibition. The results of the present invention suggest that the potent antioxidant activity exhibited by this novel class of compounds is probably due to the long-chain acyl group with the hydroxyl substitution. This is the first report of serotonin conjugates with unusual conjugation of hydroxyl fatty acids and glucose units on serotonine.

The fruits of *W. somnifera* were collected from plants grown in the greenhouses of Bioactive Natural products and Phytoceutical Laboratory at Michigan State University, East Lansing, Mich. Fruits were ground and extracted at room temperature sequentially with hexane, EtOAc, MeOH and Ammonical MeOH (pH=11). Hexane and EtOAc extracts contained β-carotene and fatty acids, as confirmed by TLC and GCMS.

The antioxidant-assay-guided fractionation of MeOH extract yielded five bioactive active fractions. Purification of active fractions by CC, reverse phase HPLC and prep. TLC yielded nine novel withanamides A-I (1-9), a new withanolide and three known withanolides.

Withanamides A (1), H (8) and I (9)-Withanamide A (1) was obtained as a pale brown amorphous powder with an $[\alpha]_D = -35°$. The HRFABMS of 1 displayed an $[M+H]^+$ ion at m/z 779.4329 (calc. 779.4330) and indicated its molecular formula as $C_{40}H_{62}N_2O_{13}$. The IR spectrum showed absorption bands at 1633, 3413 cm$^{-1}$ and-indicated the presence of amide carbonyl and hydroxyl groups in the molecule. The proton NMR signals at δ 6.66, 6.92, 6.99, and 7.15 were characteristic of a 5-oxygenated tryptamine derivative[14] and assigned to C-6, C-4, C-2 and C-7 protons, respectively. Two doublets at δ 4.38 and 4.30, integrated for one proton each, were assigned to anomeric protons and indicated that compound 1 contained a disaccharide. Two triplets observed at δ 2.84 and 3.42 were assigned to H-10 and H-11, respectively, of a tryptamine moiety. In addition to a broad singlet at δ 1.27, a triplet at δ 2.12 together with a multiplet integrated for four protons at δ 5.31 suggested the presence of an unsaturated fatty acid moiety in its structure. The terminal methyl signal at δ 1.19, appeared as a doublet, was evident of a methine carbon at C-17 in the fatty acid moiety. Also, a multiplet integrated for one proton at δ 3.79 confirmed a hydroxyl moiety at C-17. The signals at δ 2.04, 2.30 and 2.75 were assigned to allylic methylene protons in the molecule. The $^{13}$C NMR signals at δ 112.4, 112.6, 112.5, 151.0 and 133.0 were attributed to C-6, C-7, C-3, C-5 and C-9, respectively, of a 5-oxygenated tryptamine moiety. The signal at δ 176.2 indicated that the hydroxy fatty acid moiety was linked to 5-oxygenated tryptamine moiety by an amide linkage. The signals at, δ 77.7 and 22.1 were attributed to hydroxyl and methyl carbons, respectively of a side-chain. The carbon signals at δ 28.2, 28.1 and 26.5, assigned to allylic carbons, indicated the geometry of double bonds as Z in compound 1 since the allylic carbons in the E isomer appear at around 32 ppm (Spinell, A., et al., *J. Org. Chem.* 62 5471-5475 (1997); and Wenkert, E., et al., In *Topics in $^{13}$C NR spectroscopy*; Levy, G. C., Ed.; Wiley-Interscience: New York, Vol. 2, p 81-121.

Acid hydrolysis of 1 gave glucose as the only sugar in addition to serotonine and a fatty acid. The identity of glucose was confirmed by TLC comparison of the products from the hydrolysis with an authentic sample of glucose. The downfield shifts observed for C-6' by 7 ppm as compared to the C-6" showed a 1"→6' linkage of glucose moieties. By comparison of $^1$H- and $^{13}$C NMR signals with literature values, the disaccharide unit in compound 1 was identified as a diglucoside (Jayaprakasam, B., et al., *Tetrahedron* 59 841-849 (2003)).

Additional evidence of its structure was obtained from its MS fragmentation pattern, NOESY, HMBC and COSY studies. The ion at m/z 617 observed in its MS confirmed the loss of one of the glucose units from the molecular ion. The fragment at m/z 455 was assigned to the aglycone moiety and showed that the hydroxy fatty acid side chain contained 18-carbons. The diglucoside unit was placed at C-5 based on NOESY correlation of H-1' to H-4 (FIG. 1). Also, the HMBC correlations between the H-1" at δ 4.30 and C-6' at δ 69.7 confirmed a 1"→6' linkage of glucose moieties (FIG. 1). The TOCSY spectral data of compound 1 confirmed the positions of double bonds at C-6'" and C-9'", respectively. The hydroxyl proton multiplet at δ 3.79 was correlated to the methyl group in its COSY spectrum and supported the assignment of —OH at C-17 and further confirmed by HMBC correlations (FIG. 1).

The absolute configuration at C-17 was determined by Mosher's ester method (Reznaka, T., et al., *Phytochemistry* 54 635-645 (2000)). Compound 1 was reacted separately with R (−) and S (+) α-methoxytrifluorophenylacetyl chlorides (MTPA) in anhydrous pyridine. Purification of the reaction mixtures yielded the R and S-MTPA ester derivatives. The $^1$H NMR analyses of the resulting esters revealed that the C-18 methyl in S-MTPA ester appeared at a lower field than in R-MTPA ester (supporting information). Similarly, H-16 in S-MTPA ester appeared at higher field than in R-MTPA ester. The $\Delta\delta(\delta_S-\delta_R)$ value for H-18 and H-16 were +0.03 and −0.02, respectively and confirmed the configuration at C-17 as R (Reznaka, T., et al., *Phytochemistry* 54 635-645 (2000)).

Figure 2:
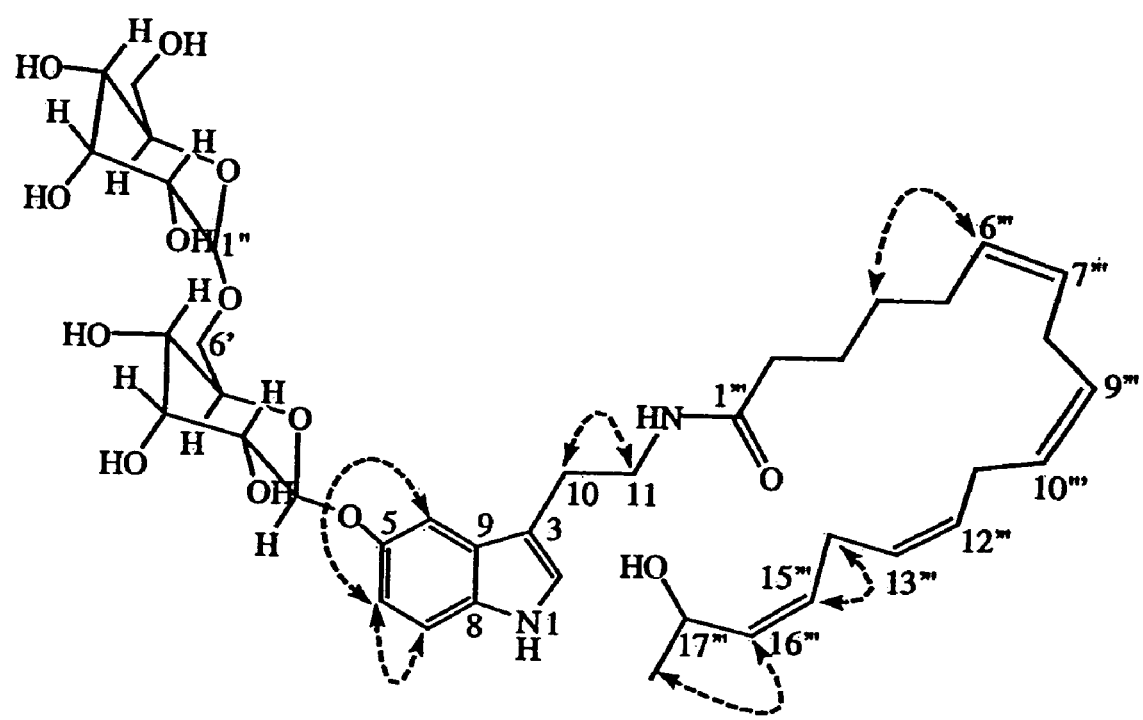
FIG. 2 is a chemical structure showing selected TOCSY (→) correlations of compound 9.

Compound 8 gave a molecular ion at m/z 775.4013. Also, the similarities observed in its $^1$H- and $^{13}$C-NMR spectra to compound 1 indicated 8 as a withanamide with two additional olefinic bonds in its side chain and further supported by an 8H multiplet at δ 5.34 and $^{13}$C NMR shifts at δ 132.6, 132.2, 131.4, 130.1, 128.7 and 128.5, respectively. A signal at δ 2.82, integrated for 6H, was assigned to methylene groups placed between olefinic bonds at C-6'" and C-7'", C-9'" and C-10'", C-12'" and C-13'" and C-15'" and C-16'". One of these double bonds was placed at C-15'" and C-16'" since the olefinic multiplet was correlated to the methyl doublet in its TOCSY spectrum (FIG. 2) and it was further evidenced by the downfield shift of terminal methyl group to 1.24 ppm. The geometry of the double bonds was deduced as Z since the allylic carbons appeared at δ 26.6, 27.0 and 28.2, respectively, in its $^{13}$C NMR spectrum. Therefore, withanamide H was confirmed to be 11,15-dehydrowithanamide A, as shown in 8.

Compound 9 also gave a similar $^1$H- and $^{13}$C-NMR spectral data to that of compound 1 as indicated by the chemical shifts for serotonine and hydroxyl-fatty acid moieties in it. The presence of two double bonds in the fatty acid moiety was confirmed by 4H multiplet at 5.33 ppm. The $[M+H]^+$ ion at m/z 941.4857 confirmed the molecular formula of 9 as $C_{46}H_{72}O_{18}N_2$. In addition, the presence of three anomeric protons appeared at δ 4.32, 4.36 and 4.39 indicated that withanamide I (9) was a triglucoside. The linkage of two glucose units, as in the case of withanamide A (1), was established as C-1"→C-6' as indicated by the downfield shift of C6' protons. A similar linkage was established for the third glucose moiety. Therefore, the glucosidic unit was established as β-D-glucopyranosyl (1"→6')-β-D-glucopyranosyl (1'"→6")-β-glucopyranoside in 9. The appearance of end methyl group as a doublet in the $^1$H-NMR of compound 9 showed that the terminal substitution of long chain fatty acid moiety in compound 9 was similar to withanamide A (1).

Figure 3:
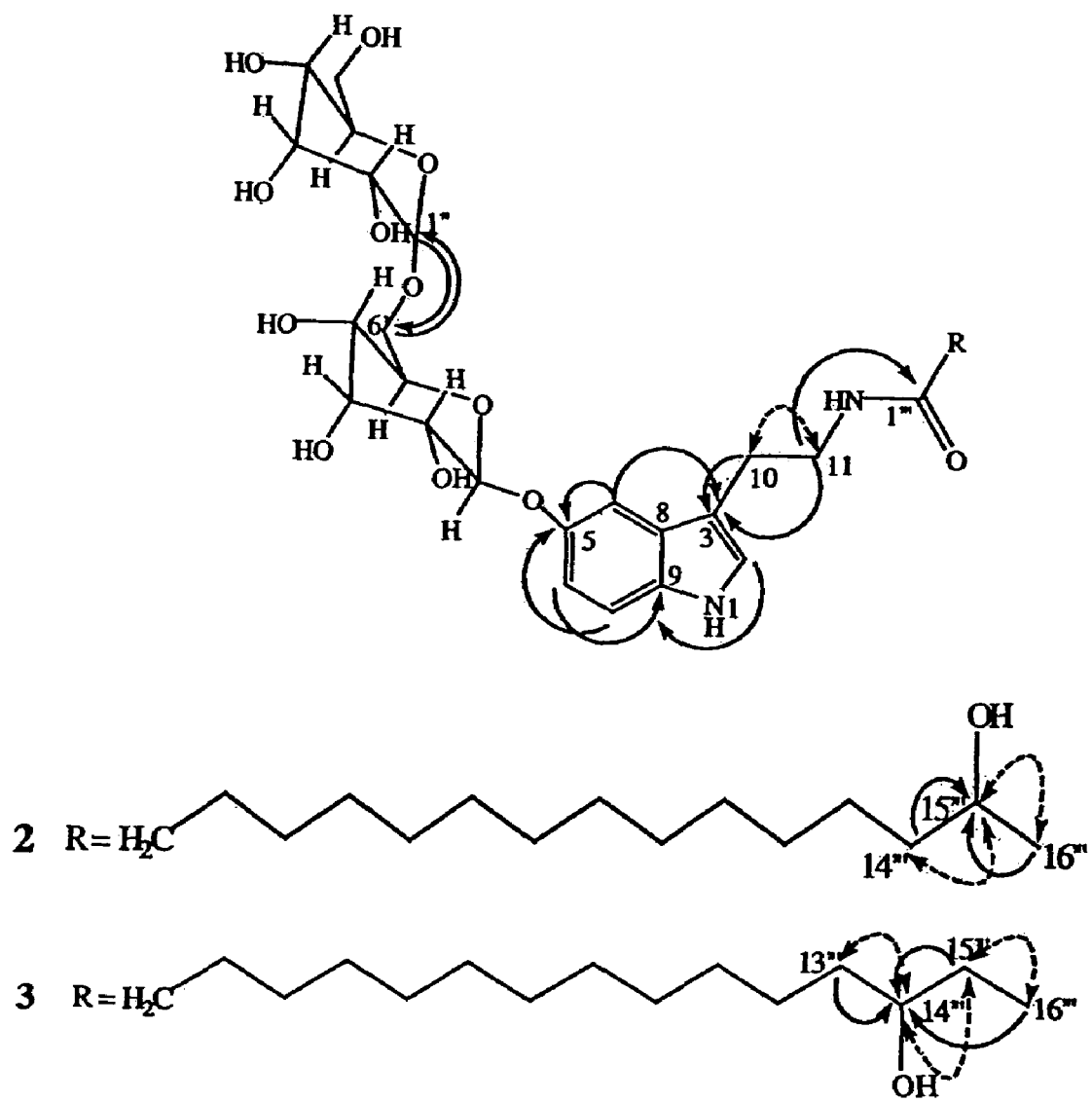
FIG. 3 shows chemical structures for significant HMBC (→) and COSY (<-→) correlations of Compounds 2 and 3.

Withanamides B-E, (2-5). Withanamide B (2), a colorless amorphous powder with an $[\alpha]_D$ of −34°, gave the $[M+H]^+$ at m/z 755.4330 and confirmed the molecular formula as $C_{38}H_{63}N_2O_{13}$ (calc. 755.4331). The $^1$H- and $^{13}$C NMR spectra of 2 were very similar to that of compound 1 with the absence of olefinic proton signal at δ 5.32. Molecular ion of 2 was 24 amu less than that of compound 1. This showed that side chain in 2 was saturated and contained only sixteen carbons. The linkage among glucose moieties was evidence as 1″→6′ by the downfield shift of C-6 to δ 69.7 and HMBC correlations observed between C-1″ and H-6′ (FIG. 3). The methyl protons were correlated to the carbon at δ 77.7 in its HMBC spectrum confirmed the —OH substitution at C-15‴ (FIG. 3). The proposed structure of 2 was confirmed by HMQC, HMBC, DTPT and NOESY experiments.

The $^1$H-NMR of compound 3 was similar to compound 2 except for a —$CH_3$ triplet at δ 0.91. In addition, it gave the molecular formula as $C_{38}H_{63}N_2O_{13}$, identical to compound 2. This indicated that compound 3 was an isomer of 2. The major difference in the $^{13}$C NMR spectrum of 3 was the upfield shift of one of the methylene groups and appeared at δ 26.3. The appearance of methyl carbon at δ 10.1 as compared to the regular fatty acids (14.0 ppm) and the downfield shift of long chain hydroxyl carbon (δ 82.0) suggested the presence of a hydroxyl group at C-14‴. The triplet at δ 0.91 showed COSY correlation with the methylene protons at δ 1.52, which correlated to a proton at δ 3.63, supported a hydroxyl moiety at C-14‴ (FIG. 3). The presence of —OH at C-14‴ was further substantiated by HMBC correlations of the methyl triplet at δ 0.91 to the hydroxyl carbon at δ 82.0 (FIG. 3). Therefore, compound 3 was confirmed as a positional isomer of 2.

The MS of compound 4 gave an [M+Na]$^+$ ion m/z 805.4462 and confirmed its molecular formula as $C_{40}H_{66}O_{13}N_2$. The $^1$H- and $^{13}$C NMR spectral data of 4 were similar to the spectral data of compound 2 and indicated a saturated side chain in the molecule. Also, the MS data confirmed that the side chain in compound 4 contained eighteen carbons.

Compound 5, a pale brown solid, gave the [M+H]$^+$ ion at m/z 783.4645 and confirmed its molecular formula as $C_{40}H_{66}N_2O_{13}$. The $^1$H NMR spectral data of 5 was similar to withanamide C (3) and indicated the presence of a saturated side chain. The methyl triplet at δ 0.91 suggested that the terminal carbons in compound 5 had a similar substitution pattern as in 3. The difference in the molecular ion by 28 amu, as compared to 3, indicated the presence of two additional methylene groups in 5. Therefore, compound 5 possessed eighteen carbons in the hydroxyl acid fatty acid side chain moiety with the hydroxyl group at C-16‴. Hence, compound 5 was a positional isomer of 4.

Withanamides F and G, (6,7). Withanamide F (6) was obtained as an inseparable mixture with fatty acid glycoside as a minor impurity. The $^1$H NMR data of 6 was similar to withanamide A (1). However, it gave a 2H multiplet at δ 5.33, assigned to a double bond, in its side chain. The appearance of a methyl triplet at δ 0.91 together with the signal for a carbon at δ 82.0 in compound 6 indicated that the terminal carbon in the fatty acid moiety had similar substitution pattern as in compounds 3 and 5. The olefinic carbons in 6 appeared at δ 130.9 and 130.7, respectively. Therefore, the olefinic moiety was assigned to C-9 since the chemical shift of these two olefinic carbons differed by 0.2 ppm. The geometry of the double bond was deduced as Z as C-8 and C-11 appeared at δ 28.1 ((Spinell, A., et al., *J. Org. Chem.* 62 5471-5475 (1997)). The HRFABMS of 6 gave a molecular ion at m/z 803.4304 [M+Na]$^+$ and further supported a C-18 fatty acid moiety in its structure.

The [M+H]$^+$ of compound 7 at m/z 753.4173 was two mass units less than the molecular ion of 2 (755.4331) and hence suggested the presence of 16C-side chain with one unsaturation in it. A 2H multiplet at δ 5.34 also supported the olefinic bond. The doublet appeared at δ 1.21, assigned to methyl protons, indicated that the —OH moiety present in the fatty acid side chain was substituted similar to the substitutions in compounds 1 and 2. Due to the paucity of sample, the $^{13}$C NMR spectrum was not informative to yield the signals for all carbons in the molecule. However, the allylic carbon signals, appeared at δ 27.0 and 28.1, confirmed the geometry of the double bond as Z. Since some of the withanamides (1, 6-9) possessed double bonds at C-9 and C-10 positions and by the biogenetic considerations, the double bond in withanamide G was tentatively assigned at C-9.

23, 24-Dihydrowithanolide VI (10): Compound 10 was isolated as a colorless amorphous powder and displayed a molecular ion at m/z 785 in its FABMS spectrum. The IR absorption bands at 3421, 1724 and 1663 cm$^{-1}$ in 10 suggested the presence of an —OH and a saturated lactone in the molecule. The HRFABMS confirmed its molecular formula as $C_{40}H_{65}O_{15}$ (M+H)$^+$ 785.4325; calc. 785.4323). The singlets at δ 0.89, 1.01, 1.25 and doublets at δ 1.17 and 1.15 were assigned to methyl groups, respectively, in its $^1$H NMR spectrum. The broad doublet at δ 5.52 and doublets at δ 4.39 and 4.36, which integrated for one proton each, were assigned to olefinic and anomeric protons, respectively. The doublet of doublet at δ 4.24 and a multiplet at δ 4.0 were assigned to H-22 and H-3, respectively. Compounds 10 and withanoside VI (11) showed similar $^1$H NMR chemical shifts (Matsuda, M., et al., *Bioorg. Med. Chem.* 9 1499-1507 (2001)). Appearance of two methyl doublets in 10 indicated that the double bond in the α,β-unsaturated δ-lactone moiety was not present. The absence of two olefinic carbons and the appearance of C=O at δ 178.9 in 10, as compared to 11, further confirmed the saturated lactone ring in the molecule. Two signals at δ 104.8 and 103.1, assigned to anometic carbons, supported a diglucosidic moiety in the molecule. The downfield shift of C-6′ protons (4.12 and 3.76 ppm), as compared to C-6″ protons (δ 3.84, 3.66), indicated a 1″→6′ linkage of two glucose moieties. Also, the downfield shift of C-6 (δ 69.7), similar to withanamides, further confirmed the glucosidic linkage as 1″→6′. Signals at δ 81.9, 58.1, 56.1, 139.1, 125.5, 75.1 and 73.6 were assigned to C-22, C-14, C-17, C-5, C-6, C-1 and C-3, respectively. Other signals appeared at δ 14.2, 14.4, 19.9, 20.5 and 21.2 were assigned to 18, 28, 19, 27 and 21 methyl carbons, respectively. The diglucoside unit was placed at C-3 by comparison of the spectra data of 10 with the spectral data of withanolides 11-13. Except for the lactone carbon signals, all other $^{13}$C NMR chemical shifts in 10 were similar to withanoside VI (11). Hence the structure of 10 was derived as 23,24-Dihydrowithanolide VI (12). The molecular ion at m/z 784, with two mass units higher than the withanoside V, further supported the proposed structure for compound 10. From the above spectral data the structure of compound 10 was derived as 23,24-Dihydrowithanolide VI.

Figure 4:
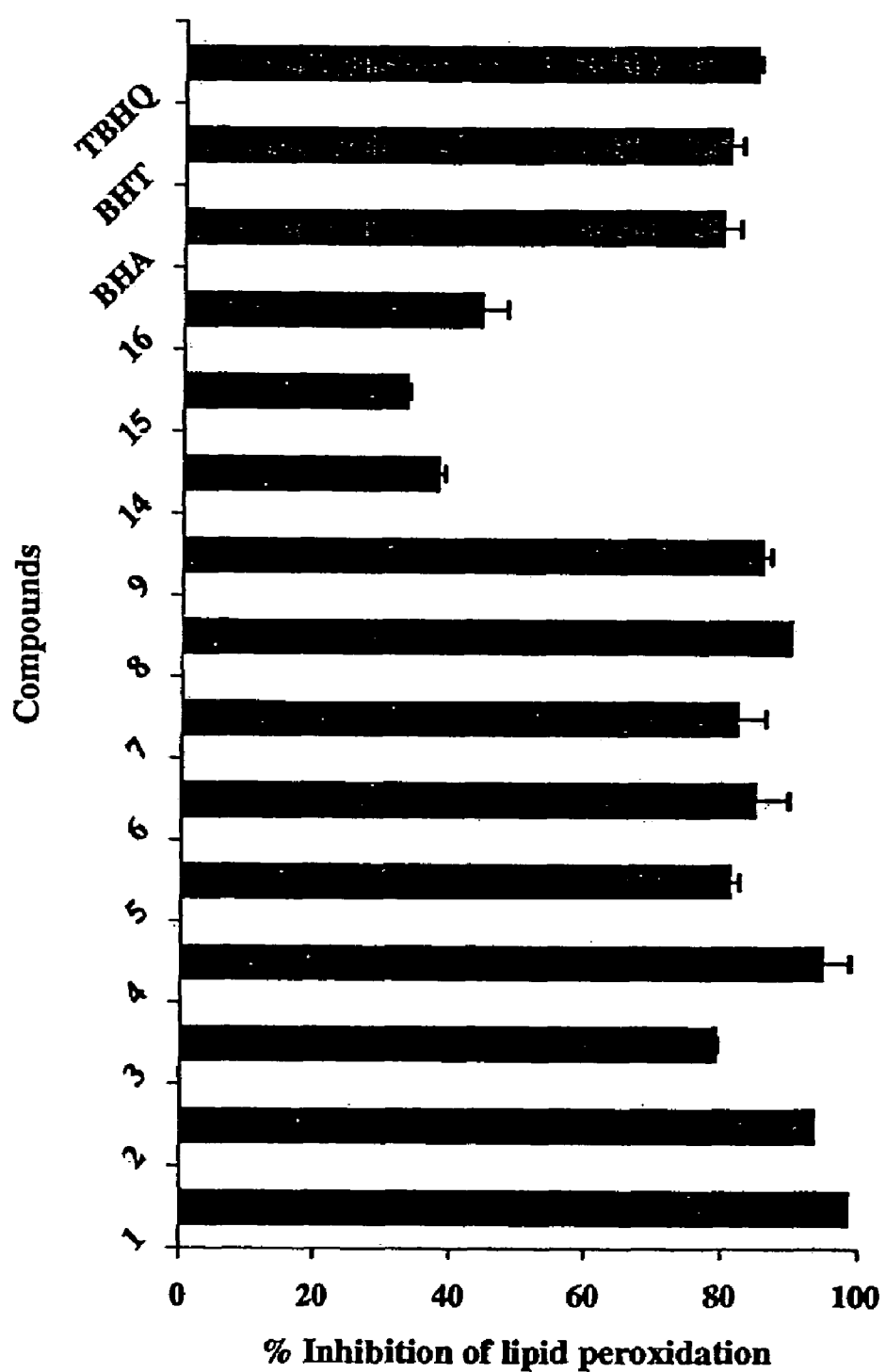
FIG. 4 is a graph showing inhibition of lipid peroxidation by compounds 1-9 and 14-16. Fluorescence intensity was monitored for 21 minutes at intervals of 3 minutes. The percentage of inhibition represented was calculated with respect to DMSO control at 21 min. The concentrations of compounds tested were 1-3, 5 and 9 at 1 μg/mL; 4, 6-8 at 0.5 μg/mL; 15 at 100 μg/mL; 16 at 50 μg/mL; 17 at 10 μg/mL. Commercial antioxidants BHA, BHT and TBHQ were tested at 1 μg/mL. Data represented indicates the mean ± one standard deviation (n=2).

Serotonine, a neurotransmitter, constituted the basic skeleton in the structure of withanamides A-I (1-9). Hence, to compare the structure and activity of these compounds, tryptamine (14),5-methoxyserotonine (15) and serotonine (16) were purchased. Compounds 1-16 and commercial antioxidants BHT, BHA and TBHQ were tested for the inhibition of lipid peroxidation by using large unilamellar vesicles (LUVs) model system (Arora, A., et al., *Free Radical Biology & Medicine* 24 1355-1363 (1998)). A dose response study was performed for all compounds and the active concentration reported in FIG. 4 was compared to the activity profiles of commercial antioxidants evaluated at 1 ppm concentration. BHA, BHT and TBHQ inhibited the lipid peroxidation by 80, 81 and 85%, respectively at 1 µg/ml (FIG. 4). Withanamide B (2) contained a saturated side chain and inhibited lipid peroxidation by 93% at 1 µg/m (FIG. 4) whereas withanamide C (3), a positional isomer of 2, showed 79% inhibition. Similarly, inhibition observed with withanamide D (4) and E (5) were 94 and 81%, respectively, at 1 µg/mL. Compounds 6 and 7 with one double bond in their side chain showed 85 and 82% inhibition, respectively, at 0.5 µg/ml. Similarly, Withanamide H (8) exhibited 90% inhibition in this assay at 0.5 µg/ml. However, Withanamide A (1), a diglucoside with two double bonds in its side chain, inhibited lipid peroxidation by 98% whereas withanamide I (9), a triglucoside, showed 86% inhibition at 1 µg/ml (FIG. 4). This indicated that the number of glycoside units also played an important role in the antioxidant activity of these compounds.

Tryptamine (14) showed 40% inhibition at 100 µg/ml and its 5-methoxy derivative, compound 15, inhibited lipid peroxidation by only 30% at 50 µg/mL. Serotonine (5-hydroxy tryptamine) hydrochloride showed 44% inhibition at 10 µg/mL. About 100% inhibition of lipid peroxidation, similar to withanamides at 1 µg/mL, was observed for compounds 14-16 when the test concentration was doubled. 5-Methoxytryptamine (15) showed higher activity than tryptamine (7) and indicated that 5-oxygenation increased the activity. Increased inhibition was observed for serotonine hydrochloride when compared to its 5-methyl derivative and suggested that the free hydroxyl at 5-position was very important for the free radical scavenging activity. Withanamides A-I, (1-9), exhibited excellent lipid peroxidation inhibitory activity equal to or better than the commercial antioxidants and far better than serotonine (FIG. 4). The serotonine nucleus and hydroxy fatty acid side chain were contributing substantially for the antioxidant activity. Among withanamides, compounds with an unsaturated side chain were more active than the saturated side chain. Compounds 2 and 4, with the hydroxyl groups at 15 and 17 position, respectively, were more active than their isomers 3 and 5 and indicated the position of the hydroxyl groups also played an important role in their antioxidant activity. The results clearly rule out the possibility of chelation of withanamides with $Fe^{2+}$ since serotonine, 5-methoxyserotonine and tryptamine were active only at much higher concentrations compared to withanamides.

Figure 5:
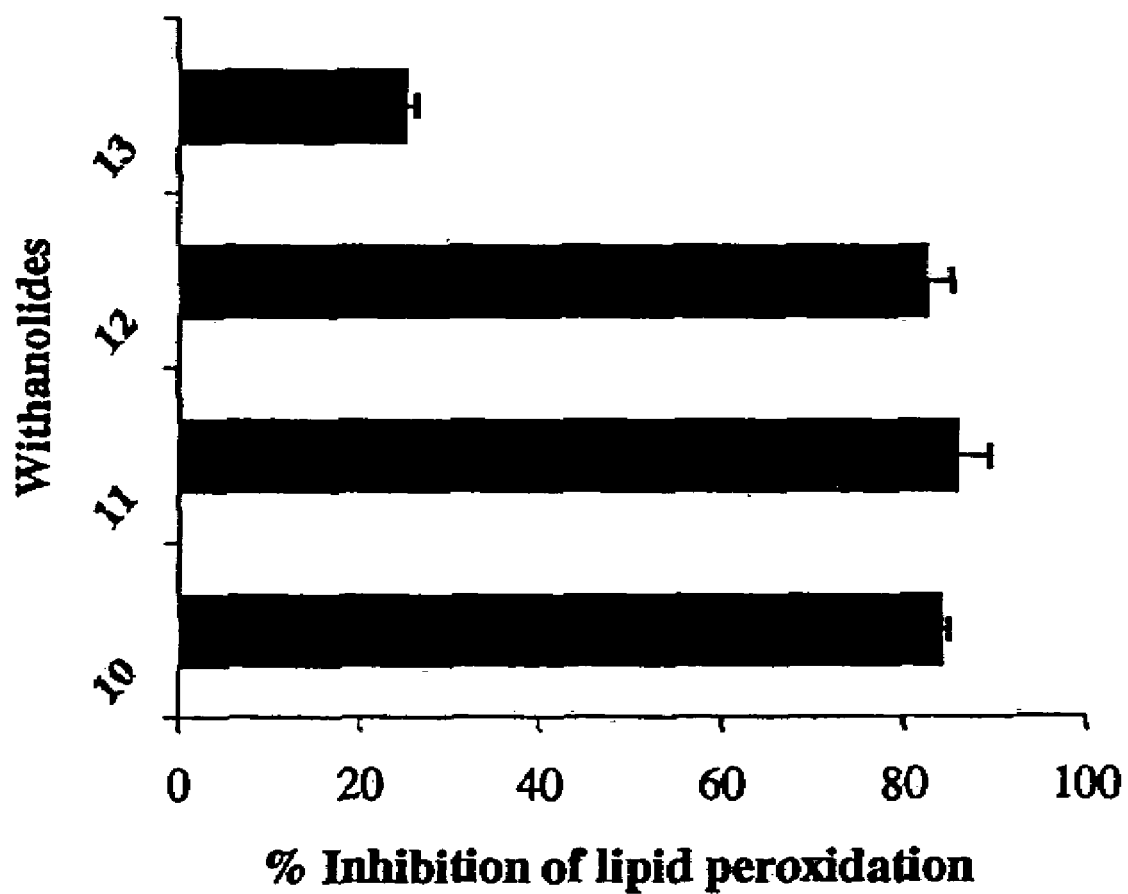
FIG. 5 is a graph showing percent inhibition of lipid peroxidation by withanolides 10-13. Compounds tested were 10 and 13 at 100 μg/mL; 12 and 11 were at 10 and 50 μg/mL, respectively. Data represented indicates the mean ± one standard deviation (n=2).

Withanolides isolated from the fruits in the present invention also inhibited lipid peroxidation (FIG. 5). Withanoside V (12), one of the major compounds isolated from *W. somnifera* seeds, showed 82.5% inhibition of lipid peroxidation at 10 ppm, whereas withanoside IV (13) inhibition was by 25% at 100 µg/mL. Withanolides VI (11) gave 86% lipid peroxidation inhibitory activity at 50 ppm and its 23,24-dihydroderivative (10) showed similar activity at 100 ppm (FIG. 5). The saturation of the lactone moiety in compound 10 decreased the activity as compared to its dehydroderivative 11 and indicated that the α,β-unsaturated δ-lactone is significant in the lipid peroxidation ability of withanolides. Compounds 11 and 13 were hydroxylated derivatives of 12. Hydroxylation at C-27 in 13 decreased the activity than the hydroxylation at C-20. This may be due to hydrogen bonding between the C27-hydroxyl and the carbonyl group of the lactone.

Withanamides A-C (1-3) and withanoside V (12) were tested for their ability to inhibit the cyclooxygenase-1 (COX-1) and cyclooxygenase-2 (COX-2) enzymes (Jayaprakasam, B., et al., *Tetrahedron* 59 841-849 (2003)) These compounds did not inhibit COX-1 or COX-2 enzymes at 100 µg/mL. They were also tested for antiproliferative activity on NCI-H460 (Lung), HCT-116 (colon), SF-268 (Central Nervous System; CNS) and MCF-7 (breast) human tumor cell lines using MTT assay (Tian, Q., et al., *Nutr. Cancer* 40 180-184 (2001)) and were inactive. This demonstrated that these compounds possess little or no toxicity.

Serotonine plays an important role in controlling many physiological functions in the human body. Its release is a determining factor in the sleep onset, pain sensitivity, blood pressure regulation and mood control. A decreased level of serotonine makes the over consumption of carbohydrates and certain food groups which lead to weight gain (Linnoila, V., et al., *J. Clin. Psychiatry* 53 46-51 (1992)) depressive symptoms, insomnia, aggressiveness and chronic head aches (Wurtman, J., *J. Clin. Psychiatry* 49 37-39 (1998)). The 5-hydroxy-L-tryptophan, precursor of serotonine, is used as an over-the-counter (OTC) drug for the treatment of various serotonine related disorders (Birdsall, T. C., *Altern Med Rev.* 3 271-280 and references cited therein (1998)). There is a potential for the conversion of the withanamides to serotonine in the stomach and the free serotonine may be absorbed if ingested orally. Therefore, the withanamides that have been isolated from *W. somnifera* seeds have the potential to increase serotonine level in the body and may be used as a supplement to deal with several disorders related to serotonine deficiency in the human. Also, two of the tryptamine analogs (sumatryptan and elitryptan) were used to treat migraine related disorders (Newman, D. J., et al., *J. Nat. Prod.* 66 1022-1037 (2003)). Therefore, withanamides can be considered as potential candidates for the treatment of migraine. Since the withanamides showed potential antioxidant activity, it can be used to prevent Alzheimer's disease and atherosclerosis.

The withanamides 1-9 are novel serotonine derivatives with novel hydroxyl-substituted fatty acids and glucose units. The withanamides 1-9 inhibited the lipid peroxidation at 0.5-1 µg/ml similar or better than BHA, BHT and TBHQ and suggested that they are better antioxidants than the commercial antioxidants. The seeds of *W. coagulence* and *W. somnifera* were used to thicken the milk in India since ancient times. It is significant to note that these compounds did not exhibit cellular toxicity in the human tumor cell assays. Therefore, *W. somnifera* seeds or the withanamides are potential candidates for the development of new and safe antioxidants for human consumption. Also, compounds 1-9 may play a greater role in the development of dietary supplements for treating various aging related disorders like Alzheimer's, Parkinson's and cardiovascular diseases using *W. somnifera* seeds.

Experimental Section

General Experimental Procedures. The HRFAB and FAB (positive ion mode) mass spectra were measured on JEOL MX 110 mass spectrometer at Michigan State University Mass Spectrometry Facility Center. Optical rotations were measured in MeOH at 20° C. on Perkin Elmer Polarimeter 341 (Shelton, Conn.). $^1H$ (500 MHz) and $^{13}C$ (125 MHz) and 2D NMR experiments were carried out on an INOVA VARIAN VRX 500 instrument using standard pulse sequences. The chemical shifts were measured in $CD_3OD$ and expressed in δ (ppm). HMBC was optimized for J=8 Hz. IR spectra were recorded on Mattson Galaxy Series FTIR 300 using WinFIRST software (Thermo Nicoloet, Madison, Wis.) spectrometer. All solvents used for isolation and purification were ACS grade. The silica gel used for MPLC was Merck Silica gel 60 (35-70 µm particle size). Si gel PTLC plates (20×20, 500 µm) were purchased from Analtech, Inc. (Newark, Del.). Recycling preparative HPLC (Japan Analytical Industry Co. model LC-20) was used with JAIGEL-ODS-C$_{18}$ Column for separation of compounds. Positive controls butylated hydroxyanisole (BHA), butylated hydroxytoluene (BHT), and tert-butylhydroquinone 9 (TBHQ), serotonine, 5-methoxyserotonine, and tryptamine were purchased from Sigma-Aldrich Co. (St. Louis, Mo.). The lipid, 1-stearoyl 2-linoleoyl sn-glycerol 3-phosphocholine (SLPC), was purchased from Avanti Polar Lipids (Alabaster, Ala.). Fluorescent probe, 3-[p-(6-phenyl)-1,3,5-hexatrienyl]-phenylpropionic acid was purchased from-Molecular Probes (Eugene, Oreg.) and R- and S-methoxy-(trifluoromethyl)phenylacetyl (MTPA) chlorides from Sigma-Aldrich Co.

Plant Material. The *Withania somnifera* plants were grown in the greenhouses of Bioactive Natural Products and Phytoceutical Laboratory at Michigan State University. Plants were grown under 12 h photoperiod at 75° F. in 1:1 mixture of loamy sand and bacto mix in 6"-plastic pots. The plants were watered and fertilized daily using 20:20:20 (N:P:K). The fully ripened seeds were collected, dried at room temperature and extracted immediately.

Extraction and Isolation. The dried and ground fruits (100 g) of *W. somnifera* were sequentially extracted with n-hexane (3×500 mL), EtOAc (3×500 mL), MeOH (5×500 mL) and ammonical MeOH (3×500 mL). Evaporation of the solvent under reduced pressure yielded n-hexane (8 g), EtOAc (2 g), MeOH (8 g) and ammonical MeOH (2 g) crude extracts. The MeOH extract (7 g) was defatted (1.5 g) with n-hexane (5×150 ml) and fractionated by silica gel medium pressure liquid chromatography (MPLC) under gradient conditions with 70% CHCl$_3$ to 80% MeOH. The 70% CHCl$_3$ eluates were collected in 10 fractions of each 40 mL, similar on TLC, pooled and concentrated to yield fractions I (300 mg). The similar fractions (8 fractions, 50 mL each) obtained from CHCl$_3$:MeOH (1:1) elution were combined and concentrated to five fraction II (100 mg). The CHCl$_3$MeOH (40:60) eluates gave 15 fractions (50 mL each) were similar, pooled, evaporated to afford fraction III (2 g). Concentration of six similar fractions (each 45 mL) from CHCl$_3$:MeOH (30:70 elution gave fraction IV (1.8 g). The 80% MeOH eluates were pooled and evaporated to afford V (200 mg).

The fractions I and II contained predominantly fatty acids as indicated by TLC. Fraction III (1.8 g) was purified by prep. HPLC using JAIGEL-ODS-C$_{18}$ column and MeOH: H$_2$O (75:25, v/v) as mobile phase at 3 mL/min. Fractions collected were A (15-30 min, 500 mg), B (31-41 min, 200 mg), C (42-56 min, 500 mg), D (58-70 min, 200 mg) and E (71-95 min, 50 mg). Fraction C was further purified by prep. HPLC using CH$_3$CN:H$_2$O (62.5:37.5, v/v) and yielded pure compounds 1 (81.95 min, 62 mg), 2 (92.0 min, 71 mg) and a fraction (104 min, 35 mg). Compounds 1 and 2 were purified again by prep. HPLC using CH$_3$CN:H$_2$O (1:1, v/v) and yielded pure compounds 1 (35 min, 50 mg) and 2 (38.0, 70 mg). The fraction at 104 min was further purified on prep. TLC using EtOAc:MeOH (9:1, v/v) and developed three times in the same mobile phase yielded pure compound 3 (R$_f$=0.5, 12 mg). Fraction D was purified by HPLC using MeOH:H$_2$O (76:24, v/v) and gave pure compound 12 (67.3 min, 150 mg). Fraction E was purified by HPLC using MeOH:H$_2$O (75:25) and yielded three fractions F (71 min, 14 mg), G (101 min, 5 mg), H (112 min, 4.0 mg).

The fraction G was purified on Prep. TLC (CHCl$_3$:MeOH, 4:1) gave compound 4 (R$_f$=0.6, 2.5 mg). Purification of fractions F and H on PTLC using CHCl$_3$:MeOH (5:1) on the mobile phase gave 5 (R$_f$=0.65, 8 mg) and 6 (R$_f$=0.58, 3.0 mg). Fraction II was subjected to HPLC using CH$_3$CN:H$_2$O (34.66, v/v) to yield five fractions fr.1 (37.0 min, 38.1 mg), fr.2 (45-70 min, 68.8 mg), fr.3 (84.4 min, 19.8 mg) and fr.4 (94.9 min, 11.4 mg).

Fr.1 was purified by prep. TLC using the mobile phase (CHCl$_3$:MeOH, 1:1, v/v) and afforded a pure withanolide 13 (R$_f$=0.40, 7.0 mg). Repeated purification of fr.4 by PTLC (CHCl$_3$:MeOH; 75:25, v/v) yielded pure compound 8 (R$_f$=0.72, 2 mg). Similarly, fr.3 was purified by PTLC (CHCl$_3$:MeOH, 70:30, v/v) yielded compounds 7 (R$_f$=0.61, 1.0 mg) and 9 (R$_f$=0.8, 0.7 mg). Purification of fr.2 by PTLC (CHCl$_3$:MeOH, 1:1, v/v) gave band of R$_f$=0.5 (25.0 mg) and further purified by prep. HPLC using CH$_3$CN:H$_2$O (33:67) as mobile phase to yield withanolides 10 (62.4 min, 6.0 mg) and 11 (70.8 min, 4.0 mg).

Withanamide A (1). Amorphous powder, [α]$_D$=−35° (C 0.0125, MeOH), IR ν$_{max}$ (KBr) 3413 (—OH), 2926, 2854, 1633 (—CONH), 1458, 1071, 1033, 626. $^1$H NMR (500 MHz, CD$_3$OD) δ 7.15 (1H, dd, J=8.5, 1.0 Hz), 6.99 (1H, s, H-2), 6.92 (1H, dd, J=2.5, 0.5 Hz, H-4), 6.66 (1H, ddd, J=9.0, 2.0 Hz, H-6), 5.31 (4H, m, H-6''',7''',9''',10'''), 4.38 (1H, d, J=8.0 Hz, H-1'), 4.30 (1H, d, J=7.5 Hz, H-1"), 4.10 (1H, dd, J=11.5, 1.0 Hz, H-6"b), 3.85 (1H, dd, J=12.0, 2.5 Hz, H-6"b), 3.79 (1H, m, H-17'''), 3.77 (1H, dd, J=11.5, 5.0 Hz, H-6'a), 3.65 (1H, dd, J=12.0, 5.5 Hz, H-6"a), 3.42 (2H, t, J=7.5 Hz, H-11), 3.40 (1H, m, H-5'), 3.39 (2H, m, H-4', H-4"), 3.27-3.38 (2H, m, H-5", H-3", H-3'), 3.20 (1H, d,J=9.0, 8.0 Hz, H-2"), 3.15 (1H, dd, J=9.0, 8.0 Hz, H-2'), 2.84 (2H, t, J=7.0 Hz, H-10), 2.75 (2H, t, J=6.5 Hz, H-8'''), 2.12 (2H, t, J=7.5 Hz, H-2'''), 2.04 (4H, m, H-5''', 11'''), 1.54 (2H, m, H-3'''), 1.42 (2H, m, H-4'''), 1.32 (2H, m, H-16'''), 1.27 (8H, br. s, H-12'''-H-15'''), 1.19 (3H, d, J=6.0 Hz, H-18'''). $^{13}$C NMR (125 MHz, CD$_3$OD) δ 176.2 (C-1'''), 151.0 (C-5), 133.0 (C-8), 130.9 (C-10''') 130.8 (C-7'''), 129.4 (C-9), 129.2 (C-9'''), 129.0 (C-6'''), 124.2 (C-2), 112.6 (C-7), 112.5 (C-3), 112.4 (C-6), 104.7 (C-1"), 104.0 (C-1'), 103.5 (C-4), 77.9 (C-3',3",5"), 77.7 (C-17"), 76.8 (C-5'), 75.2 (C-2"), 75.0 (C-2'), 71.6 (C-4"), 71.4 (C-4'), 69.7 (C-6'), 62.7 (C-6"), 41.2 (C-11), 37.3 (C-16'''), 37.2 (C-2'''), 30.6-30.1 (C-12'''-15'''), 30.0 (C-4'''), 28.2 (C-11'''), 28.1 (C-5'''), 27.0 (C-3'''), 26.5 (C-8'''), 26.3 (C-10), 22.1 (C-18'''). HRFABMS 779.4329 (calcd for C$_{40}$H$_{63}$N$_2$O$_{13}$ (M+H)$^+$, 779.4330). FABMS (m/z) 779 [M+H]$^+$, 778 [M]$^+$, 617, 455, 437, 175, 160, 159, 146.

Withanamide B (2). Amorphous powder, [α]$_D$=−34° (C 0.0125, MeOH), IR ν$_{max}$ (KBr) 3372 (—OH), 2924, 2853, 1632 (—CONH), 1463, 1371, 1071, 1031, 631. $^1$H NMR (500 MHz, CD$_3$OD) δ 7.15 (1H, dd, J=8.5, 0.5 Hz, H-7), 7.0 (1H, s, H-2), 6.94 (1H, dd, J=2.5, 0.5 Hz, H-4), 6.66 (1H, dd, J=9.0, 2.5 Hz, H-6), 4.40 (1H, d, J=8.0 Hz, H-1"), 4.32 (1H, d, J=7.5 Hz, H-1'), 4.11 (1H, dd, J=12.0, 2.0 Hz, H-6"b), 3.87 (1H, dd, J=12.0, 2.0 Hz, H-6"b), 3.79 (1H, m, H-15'''), 3.78 (1H, dd, J=12.0, 5.5 Hz, H-6'a), 3.67 (1H, dd, J=12.0, 5.5 Hz, H-6"a), 3.44 (2H, t, J=7.0 Hz, H-11), 3.41 (2H, m, H-4", 5'), 3.40 (1H, m, H-4'), 3.25-3.38 (2H, m, H-5", H-3", H-3'), 3.24 (1H, dd, J=9.0, 8.0 Hz, H-2"), 3.17 (1H, dd, J=9.0, 8.0 Hz, H-2'), 2.85 (2H, t, J=8.0 Hz, H-10), 2.13 (2H, t, J=7.0 Hz, H-2'''), 1.55 (2H, m, H-3'''), 1.39 (4H, m, H-4''', H-14'''), 1.26 (18H, br. s, H-5'''-H-13'''), 1.20 (3H, d, J=6.5 Hz, H-16'''); $^{13}$C NMR (125 MHz, CD$_3$OD) δ 176.2 (C-1'''), 151.0 (C-5), 133.0 (C-8), 129.4 (C-9), 124.2 (C-2), 112.6 (C-7), 112.4 (C-3), 112.3 (C-6), 104.7 (C-1"), 103.9 (C-1'), 103.5 (C-4), 77.9 (3", 5"), 77.8 (C-3'), 77.7 (C-15'''), 76.8 (C-5'), 75.2 (C-2"), 75.0 (C-2'), 71.5 (C-4"), 71.4 (C-4'), 69.7 (C-6'), 62.7 (C-6"), 41.2 (C-11), 37.6 (C-14'''), 37.2 (C-2'''), 30.8-30.2 (C-4'''-13'''), 27.0 (C-3'''), 26.3 (C-10), 22.0 (C-16'''). HRFABMS 755.4331 (calcd for C$_{38}$H$_{63}$N$_2$O$_{13}$ (M+H)+, 755.4330). FABMS (m/z) 777 [M+Na]+, 755 [M+H]+, 754 [M]+, 593, 431, 413, 396, 160, 146.

Withanamide C (3). Amorphous powder, [α]$_D$=−34° (C 0.01, MeOH), IR ν$_{max}$ (KBr) 3422 (—OH), 2924, 2853, 1633 (—CONH), 1459, 1071, 1032, 631. $^1$H NMR (500 MHz, CD$_3$OD) δ 7.15 (1H, dd, J=8.5, 0.5 Hz, H-7), 6.99 (1H, s, H-2), 6.92 (1H, dd, J=2.0, 0.5 Hz, H-4), 6.65 (1H, dd, J=8.5, 2.0 Hz, H-6), 4.40 (1H, d, J=8.0 Hz, H-1″), 4.30 (1H, d, J=8.0 Hz, H-1′), 4.10 (1H, dd, J=12.0, 2.0 Hz, H-6′b), 3.86 (1H, dd, J=12.0, 2.5 Hz, H-6″b), 3.79 (1H, dd, J=12.0, 6.0 Hz, H-6′a), 3.66 (1H, dd, J=12.0, 5.5 Hz, H-6″a), 3.63 (1H, m, H-14‴), 3.44 (2H, t, J=7.0 Hz, H-11), 3.40 (1H, m, H-4′), 3.39 (1H, t, J=7.5 Hz, H-5′), 3.25-3.37 (4H, m, H-5″, 4″, 3′, 4′), 3.20 (1H, dd, J=9.0, 7.5 Hz, H-2″), 3.16 (1H, dd, J=9.0, 7.5 Hz, H-2′), 2.85 (2H, t, J=7.5 Hz, H-10), 2.14 (2H, t, J=7.5 Hz, H-2‴), 1.56 (4H, m, H-3‴, 15‴), 1.52 (2H, m, H-13‴), 1.39 (4H, m, H-4‴ & H-14‴), 1.27 (18H, br. s, H-4‴-H-12‴), 0.91 (3H, t, J=7.5 Hz, H-16‴); $^{13}$C NMR (125 MHz, CD$_3$OD) δ 176.3 (C-1‴), 151.1 (C-5), 133.1 (C-8), 129.5 (C-9), 124.2 (C-2), 112.6 (C-7), 112.5 (C-3), 112.4 (C-6), 104.9 (C-1″), 103.6 (C-1′), 103.5 (C-4), 82.0 (C-14‴), 78.1 (C-5″), 78.0 (C-3′, 3″), 77.0 (C-5′), 75.3 (C-2″), 75.2 (C-2′), 71.7 (C-4″), 71.6 (C-4′), 69.9 (C-6′), 62.8 (C-6″), 41.2 (C-11), 37.2 (C-2‴), 34.5 (C-13‴), 31.0-28.6 (C-4‴-12‴), 27.0 (C-3‴), 26.3 (C-15‴), 26.0 (C-10), 10.1 (C-16‴). HRFABMS 755.4331 (calcd for C$_{38}$H$_{63}$N$_2$O$_{13}$ (M+H)+, 755.4330). FABMS (m/z) 777 [M+Na]+, 755 [M+H]+, 754 [M]+, 431, 413, 396, 160, 159, 146.

Withanamide D (4). Amorphous powder. IR ν$_{max}$ (KBr) 3402 (—OH), 2923, 2852, 1636 (—CONH), 1464, 1381, 1071, 1040, 630. $^1$H NMR (500 MHz, CD$_3$OD) δ 7.14 (1H, dd, J=9.0, 0.5 Hz, H-7), 6.99 (1H, s, H-2), 6.93 (1H, dd, J=2.5, 0.5 Hz, H-4), 6.65 (1H, dd, J=9.0, 2.5 Hz, H-6), 4.39 (1H, d, J=8.0 Hz, H-1″), 4.32 (1H, d, J=8.0, Hz, H-1′), 4.10 (1H, dd, J=11.5, 2.0 Hz, H-6′b), 3.86 (1H, dd, J=12.0, 2.5 Hz, H-6″b), 3.79 (1H, m, H-17‴), 3.79 (1H, dd, J=12.0, 5.5 Hz, H-6′a), 3.66 (1H, dd, J=12.0, 5.5 Hz, H-6″a), 3.44 (2H, t, J=7.0 Hz, H-11), 3.41 (2H, m, H-4″, 5′), 3.40 (1H, m, H-4′), 3.25-3.36 (4H, m, H-3′, 3″, 5′, 5″), 3.20 (1H, dd, J=9.0, 8.0 Hz, H-2″), 3.15 (1H, dd, J=9.0, 8.0 Hz, H-2′), 2.86 (2H, t, J=7.0 Hz, H-10), 2.14 (2H, t, J=7.0 Hz, H-2‴), 1.57 (2H, m, H-3‴), 1.40 (2H, m, H-16‴), 1.28 (24H, br. s, H-4‴-H-15‴), 1.21 (3H, d, J=6.0 Hz, H-18‴); $^{13}$C NMR (125 MHz, CD$_3$OD) δ 176.3 C-1‴), 151.1 (C-5), 133.1 (C-8, 129.5 (C-9), 124.2 (C-2), 112.6 (C-7), 112.5 (C-3), 112.4 (C-6), 104.8 (C-1″), 104.0 (C-1′), 103.5 (C-4), 78.0 (C-3′, 3″, 5″), 77.8 (C-17′), 77.0 (C-5′), 75.3 (C-2″), 75.1 (C-2′), 71.6 (C-4′), 71.5 (C-4″), 69.8 (C-6′), 62.8 (C-6″), 41.2 (C-11), 37.8 (C-16‴), 37.2 (C-2‴), 30.9-30.2 (C-4‴-15‴), 27.0 (C-3‴), 26.3 (C-10), 22.1 (C-18‴). HRFABMS 805.4462 (calcd for C$_{40}$H$_{67}$N$_2$O$_{13}$Na, 805,4463). FABMS (m/z) 805 [M+Na]+, 783 [M+H]+, 643, 459, 441, 371, 363, 347, 160, 159.

Withanamide E (5). Amorphous powder. $^1$H NMR (500 MHz, CD$_3$OD) δ 7.15 (1H, dd, J=8.5 Hz, H-7), 7.0 (1H, s, H-2), 6.93 (1H, dd, 2.0, 0.5 Hz; H-4), 6.65 (1H, dd, J=8.5, 2.0 Hz, H-6), 4.40 (1H, d, J=8.0 Hz, H-1″), 4.30 (1H, d, J=8.0 Hz, H-1′), 4.10 (1H, dd, J=12.0, 2.0 Hz, H-6′b), 3.86 (1H, dd, J=12.0, 2.5 Hz, H-6″b), 3.78 (1H, dd, J=12.0, 6.0 Hz, H-6′a), 3.66 (1H, dd, J=12.0, 5.5 Hz, H-6″a), 3.63 (1H, t, J=6.0 Hz, H-14‴), 3.44 (2H, t, J=7.5 Hz, H-11), 3.40 (1H, m, H-4′), 3.39 (1H, t, J=7.5 Hz, H-5′), 3.25-3.37 (4H, m, H-5″, 4″, 3′, 4′), 3.20 (1H, dd, J=9.0, 7.5 Hz, H-2″), 3.16 (1H, dd, J=9.0, 7.5 Hz, H-2′), 2.85 (2H, t, J=7.5 Hz, H-10), 2.14 (2H, t, J=7.5 Hz, H-2‴), 1.56 (4H, m, H-3‴, 17‴), 1.52 (2H, m, H-15‴), 1.27 (22H, br. s, H-4‴-H-14‴), 0.91 (3H, t, J=7.5 Hz, H-18‴). HRFABMS 783.4645 (calcd for C$_{40}$H$_{67}$O$_{13}$N$_2$ 783.4644). FABMS (m/z) 805 [M+Na]+, 783 [M+H]+, 765, 621, 459, 441, 282, 202, 175, 160, 159, 146.

Withanamide F (6). Amorphous powder. IR ν$_{max}$ (KBr) 3402 (—OH), 2926, 2853, 1635 (—CONH), 1456, 1368, 1069, 1036, 615. $^1$H NMR (500 MHz, CD$_3$OD) δ 7.14 (1H, dd, J=8.5, 0.5 Hz, H-7), 6.99 (1H, s, H-2), 6.92 (1H, dd, J=2.5, 0.5 Hz, H-4), 6.65 (1H, dd, J=8.5, 2.5 Hz, H-6), 5.33 (2H, m, H-9‴, 10‴), 4.39 (1H, d, J=7.0 Hz, H-1″), 4.30 (1H, d, J=7.5 Hz, H-1′), 4.09 (1H, dd, J=11.5, 2.0 Hz, H-6′b), 3.86 (1H, dd, J=11.5, 2.0 Hz, H-6″b), 3.78 (1H, dd, J=11.5, 5.5 Hz, H-6′a), 3.66 (1H, dd, J=11.5, 5.5 Hz, H-6″a), 3.62 (1H, t, J=6.0, H-16‴), 3.44 (2H, t, J=7.5 Hz, H-11), 3.41 (2H, m, H-4″, 5′), 3.40 (1H, m, H-4′), 3.25-3.36 (4H, m, H-3′,3″,5′, 5″), 3.20 (1H, dd, J=9.0, 8.0 Hz, H-2″), 3.15 (1H, dd, J=9.0, 8.0 Hz, H-2′), 2.85 (2H, t, J=7.0 Hz, H-10), 2.14 (2H, t, J=7.5 Hz, H-2‴), 2.02 (4H, m, H-8‴, 11‴), 1.55 (8H, m, H-3‴, 16‴, 7‴, 12‴), 1.28 (24H, br. s, H-4‴-6‴, H-13‴-15‴), 0.91 (3H, t, J=7.5 Hz, H-18‴). $^{13}$C NMR (125 MHz, CD$_3$OD) δ 176.3 (C-1‴), 151.2 (C-5), 133.1 (C-8), 130.9 (C-10‴), 130.8 (C-9‴), 129.5 (C-9), 124.2 (C-2), 112.6 (C-7), 112.5 (C-3), 112.4 (C-6), 104.9 (C-1″), 103.6 (C-1′), 103.5 (C-4), 82.0 (C-16‴), 78.0 (C-3′, 3″, 5″), 77.0 (C-5′), 75.3 (C-2″), 75.1 (C-2′), 71.7 (C-4″), 71.6 (C-4′), 69.9 (C-6′), 62.8 (C-6″), 41.2 (C-11), 37.2 (C-17‴), 37.2 (C-2‴), 30.8-30.1 (C-5‴-7‴, C-12‴-C15‴), 30.2 (C-4‴), 28.2 (C-11‴), 28.1 (C-8‴) 27.0 (C-3‴), 26.5 (C-5‴), 26.3 (C-10), 10.2 (C-18‴). HRFABMS 803.4304 (calcd for C$_{40}$H$_{64}$O$_{13}$N$_2$Na, 803.4306). FABMS (m/z) 803 [M+Na]+, 781 [M+H]+, 641, 619, 457, 439, 393, 347, 160, 159, 146.

Withanamide G (7). Amorphous powder. $^1$H-NMR (500 MHz, CD$_3$OD) δ 7.15 (1H, d, J=9.0 Hz, H-7), 7.0 (1H, s, H-2), 6.92 (1H, d, J=2.0 Hz, H-4), 6.65 (1H, dd, J=9.0, 2.0 Hz, H-6), 5.34 (2H, m, H-9‴, 10‴), 4.39 (1H, d, J=7.5 Hz, H-1″), 4.31 (1H, d, J=7.5 Hz, H-1′), 4.10 (1H, dd, J=12.0, 2.0 Hz, H-6′b), 3.85 (1H, dd, J=12.0, 2.5 Hz, H-6″b), 3.79 (1H, m, H-15‴), 3.78 (1H, dd, J=12.0, 5.0 Hz, H-6′a), 3.66 (1H, dd, J=12.0, 5.0 Hz, H-6″a) 3.44 (2H, t, J=7.5 Hz, H-11), 3.41 (2H, m, H-4″, 5′), 3.40 (1H, m, H-4′), 3.25-3.38 (4H, m, H-5″, H-3″, H-3′), 3.24 (1H, dd, J=9.0, 8.0 Hz, H-2″), 3.16 (1H, dd, J=9.0, 8.0 Hz, H-2′), 2.85 (2H, t, J=7.0 Hz, H-10), 2.14 (2H, t, J=7.5 Hz, H-2‴), 1.55 (2H, m, H-3‴, H-14‴), 2.03 (4H, m, H-2‴), 1.39 (2H, m, H-3‴), 1.28 (14H, br. s, H-5‴-H-13‴), 1.21 (3H, d, J=6.5 Hz, H-16‴). HRFABMS 753.4173 (calcd for C$_{38}$H$_{61}$O$_{13}$N$_2$, 753.4174). FABMS (m/z) 775 [M+Na]+, 753 [M+H]+, 596, 155, 114.

Withanamide H (8). Amorphous powder. $^1$H NMR (500 MHz, CD$_3$OD) δ 7.14 (1H, d, J=8.5 Hz, H-7), 6.99 (1H, s, H-2), 6.92 (1H, d, J=2.5 Hz, H-4), 6.65 (1H, dd, J=8.5, 2.5 Hz, H-6), 5.34 (8H, m, H-6‴, 7‴, 9‴, 10‴, 11‴, 12‴, 14‴, 15‴), 4.33 (1H, d, J=8.0 Hz, H-1″), 4.27 (1H, d, J=8.0 Hz, H-1′), 4.10 (1H, dd, J=12.0, 2.0 Hz, H-6′b), 3.85 (1H, dd, J=12.0, 2.5 Hz, H-6″b), 3.79 (1H, m, H-15‴), 3.78 (1H, dd, J=12.0, 5.0 Hz, H-6′a), 3.66 (1H, dd, J=12.0, 5.0 Hz, H-6″a), 3.44 (2H, t, J=7.5 Hz, H-11), 3.41 (2H, m, H-4″, 5′), 3.40 (1H, m, H-4′), 3.25-3.38 (4H, m, H-5″, H-3″, H-3′), 3.24 (1H, dd, J=9.0, 8.0 Hz, H-2″), 3.16 (1H, dd, J=9.0, 8.0 Hz, H-2′), 2.85 (2H, t, J=7.0 Hz, H-10), 2.82 (6H, m, H-8‴, 11‴, 14‴), 2.14 (2H, t, J=7.5 Hz, H-2‴), 2.07 (2H, m, 5‴), 1.55 (2H, m, H-3‴), 1.28 (2H, br. s, H-4‴), 1.24 (3H, d, J=6.5 Hz, H-6‴). $^{13}$C NMR (125 MHz, CD$_3$OD) δ 176.3 (C-1‴), 151.2 (C-5), 133.2 (C-8), 132.6 (C-9‴), 132.2 (C-6‴), 131.4 (C-7‴, 10‴), 130.1 (C-15‴), 129.5 (C-9), 128.7 (C-12‴, 13‴) 128.5 (C-6‴, 15‴), 124.2 (C-2), 112.6 (C-7), 112.5 (C-3) 112.4 (C-6), 104.9 (C-1″), 100.9 (C-1′), 103.5 (C-4), 78.0 (C-3′, 3″, 5″), 77.7 (C-17‴), 76.8 (C-5′), 75.0 (C-2″), 74.9 (C-2′), 71.6 (C-4″), 71.3 (C-4′), 69.6 (C-6′), 62.8 (C-6″), 41.2 (C-11), 37.2 (C-2‴), 30.7 (C-4‴), 28.2 (C-5′), 27.0

(C-3'''), 26.6 (C-8''', 11''', 12'''), 26.3 (C-10), 21.9 (C-18'''). HRFABMS 775.4013 (calcd for $C_{40}H_{59}O_{13}N_2$, 775.4017). FABMS (m/z) 799 [M+Na]$^+$, 775 [M+H]$^+$, 591, 435, 411, 160, 159, 146.

Withanamide I (9). Amorphous powder. $^1$H NMR (500 MHz, CD$_3$OD) δ 7.14 (1H, d, J=8.5, 0.5 Hz, H-7), 6.99 (1H, s, H-2), 6.93 (1H, d, 2.5 Hz, H-4), 6.65 (1H, dd, J=8.5, 2.0 Hz, H-6), 5.33 (4H, m, H-6'', 7''', 9''', 10'''), 4.39 (1H, d, J=7.5 Hz, H-1''), 4.36 (1H, d, J=8.0 Hz, H-1'''), 4.32 (1H, d, J=8.0 Hz, H-1'), 4.15 (1H, bd, J=12.0 Hz, H-6''b), 4.09 (1H, br. d, J=12.0 Hz, H-6'b), 3.86 (1H, dd, J=12.0, 2.0 Hz, H-6'''b), 3.79 (1H, m, H-15'''), 3.78 (1H, dd, J=12.0, 5.5 Hz, H-6'a), 3.75 (1H, dd, J=11.0, 6.0 Hz, H-6'a), 3.66 (1H, dd, J=12.0, 5.0 Hz, H-6'''a), 3.44 (2H, t, J=7.5 Hz, H-11), 3.41 (3H, m, H-4'', 4''', 5'), 3.40 (1H, m, H-4'), 3.25-3.38 (5H, m, H-5'', 5''', 3''', 3'', 3'), 3.24 (2H, dd, J=9.0, 8.0 Hz, H-2'', 2'''), 3.16 (1H, dd, J=9.0, 8.0 Hz, H-2'), 2.85 (2H, t, J=7.0 Hz, H-10), 2.77 (2H, t, J=6.0 Hz, H-8'''), 2.15 (2H, t, J=7.5 Hz, H-2'''), 1.28 (10H, br s, H-5'''-H-13'''), 2.04 (4H, m, H-5''', 11'''), 1.56 (2H, m, H-3'''), 1.21 (3H, d, J=6.5 Hz, H-6'). HRFABMS 941.4857 (calcd for $C_{46}H_{73}O_{18}N_2$, 941.4859). FABMS (m/z) 963 [M+Na]$^+$, 941 [M+H]$^+$, 617, 455, 437, 316, 160, 159, 146.

23,24-Dihydrowithanolide VI (10). Colorless, amorphous powder. IR ν$_{max}$ (KBr) 3421 (—OH), 2936, 1724, 1663, 1460, 1384, 1073, 1043. $^1$H NMR (500 MHz, CD$_3$OD) δ 5.52 (1H, br d, J=5.0 Hz, H-6), 4.39 (1H, d, J=8.0 Hz, H-1''), 4.24 (1H, dd, J=11.5, 2.5 Hz, H-22), 4.36 (1H, d, J=8.0 Hz, H-1'), 4.12 (1H, dd, J=11.5, 2.5 Hz, H-6'b), 4.0 (1H, m, H-3), 3.86 (1H, dd, J=11.5 2.0 Hz, H-6''b), 3.80 (1H, m, H-1), 3.76 (1H, dd, J=11.5, 6.0 Hz, H-6'a), 3.66 (1H, dd, J=12.0 6.0 Hz, H-6''a), 3.41 (3H, m, H-4'', 5', H-11), 3.40 (1H, m, H-4'), 3.25-3.38 (3H, m, H-5'', H-3'', H-3'), 3.24 (1H, dd, J=9.0, 8.0 Hz, H-2''), 3.16 (1H, dd, J=9.0, 8.0 Hz, H-2'), 1.24 (3H, s, Me-28), 1.17 (3H, d, J=6.5 Hz, Me-27), 1.15 (3H, d, J=6.5 Hz, Me-27), 1.01 (3H, s, Me-19), 0.89 (3H, s, Me-18). $^{13}$C NMR (125 MHz, CD$_3$OD) δ 178.9 (C-26), 139.15 (C-5), 125.5 (C-6), 104.8 (C-1''), 103.1 (C-1'), 81.9 (C-22), 78.0 (C-3', 3''), 77.9 (C-5''), 77.0 (C-5'), 76.5 (C-20), 75.5 (C-2''), 75.2 (C-2'), 75.1 (C-1), 73.6 (C-3), 71.7 (C-4''), 71.6 (c-4'0, 69.7 (C-6'), 62.8 (C-6''), 58.1 (C-14), 56.1 (C-17), 44.0 (c-26), 42.7 (C-13), 42.5 (C-10), 41.4 (C-9), 41.1 (C-12), 39.2 (C-4), 37.8 (C-2), 32.8 (C-25), 32.7 (C-23), 32.6 (C-7), 32.0 (C-8), 25.0 (C-15), 23.0 (C-16), 21.2 (C-21), 20.5 (C-27), 19.9 (C-19), 14.4 (C-28), 14.2 (C-18). HRFABMS 785.4325 (calcd for $C_{40}H_{65}O_{15}$, 785.4323). FABMS m/z 807 [M+Na]$^+$, 785. 623, 605, 587, 443, 425, 407, 255.

Compounds 11-13. The structures of compounds 11-13 were elucidated by $^1$H and $^{13}$C NMR data and their identity was confirmed by comparing the spectral data with the published results (Jayaprakasam, B., et al., *Tetrahedron* 59 841-849 (2003); and Matsuda, M., et al., *Bioorg. Med. Chem.* 9 1499-1507 (2001)).

Preparation of R- and S-MTPA Esters of Compound 1

A mixture of compound 1 (1.5 mg) and R-(–)-Methoxy trifluorophenyl acetyl chloride (R-MTPA) in pyridine was stirred with dimethylaminopyridine (DMAP) (5 h) at room temperature. The solvent was evaporated and residue obtained was purified over PTLC using CHCl$_3$:MeOH (9:1, v/v) to yield R-MTPA ester (1.0 mg). Similarly, compound 1 (1.2 mg) was treated with S-(+)-Methoxytrifluorophenyl acetyl chloride and the purification of the resulting product gave S-MTPA ester (0.9 mg).

Antioxidant Assay

Compounds 1-16 were tested for their inhibition of lipid peroxidation using Large Unilamellar Vesicles (Liposome suspension) according to the published procedure (Arora, A., et al., *Free Radical Biology & Medicine* 24 1355-1363 (1998)). The liposome suspension was prepared by mixing the phospholipid 1-stearoyl-2-linoleoyl-sn-glycero-3-phosphocoline (SLPC) and a fluorescence probe [3-[p-(6-phenyl)-1,3,5-hexatrienylph-enylpropionic acid (DPH-PA). The final assay volume was 2 mL and consisted HEPES (100 µL), 1M NaCl (200 µL), N$_2$-sparged water (1.64 ml), test sample or DMSO (20 µL) and liposome suspension (20 µL). The peroxidation was initiated by the addition of 20 µl of FeCl$_2$. 4H$_2$O (0.5 mM). The fluorescence was monitored at 0, 1, 3 and every 3 min up to 21 min using a Turner Model 450 Digital fluorometer. The decrease in fluorescence intensity over the time (21 min) indicated the rate of peroxidation. The percentage of lipid peroxidation was calculated with respect to DMSO solvent control. Stock solutions of the samples were prepared at 100 µg/ml and diluted further for the assay.

Pharmaceutical Compositions

In pharmaceutical compositions, the withanamide or withanolide is inhibitory at a dosage of 1 to 1,000 micrograms per milliliter or gram. In a preferred embodiment, one or more of the withanamides or withanolides for treating a patient are provided to the patient at an inhibitory dose in a pharmaceutically acceptable carrier. As such, the withanamides or withanolides are processed with pharmaceutical carrier substances by methods well known in the art such as by means of conventional mixing, granulating, coating, suspending and encapsulating methods, into the customary preparations for oral or rectal administration. Thus, withanolide or withanamide preparations for oral application can be obtained by combining one or more of the anthraquinones with solid pharmaceutical carriers; optionally granulating the resulting mixture; and processing the mixture or granulate, if desired and/or optionally after the addition of suitable auxiliaries, into the form of tablets or dragee cores.

Suitable pharmaceutical carriers for solid preparations are, in particular, fillers such as sugar, for example, lactose, saccharose, mannitol or sorbitol, cellulose preparations and/or calcium phosphates, for example, tricalcium phosphate or calcium hydrogen phosphate; also binding agents, such as starch paste, with the use, for example, of maize, wheat, rice or potato starch, gelatine, tragacanth, methyl cellulose, hydroxyprdpylmethyl cellulose, sodium carboxymethyl cellulose and/or polyvinylpyrrolidone, esters of polyacrylates or polymethacrylates with partially free functional groups; and/or, if required, effervescent agents, such as the above-mentioned starches, also carboxymethyl starch, cross-linked polyvinylpyrrolidone, agar, or alginic acid or a salt thereof, such as sodium alginate. Auxiliaries are primarily flow-regulating agents and lubricating agents, for example, silicic acid, talcum, stearic acid or salts thereof, such as magnesium stearate or calcium stearate. Dragee cores are provided with suitable coatings, optionally resistant to gastric juices, whereby there are used, inter alia, concentrated sugar solutions optionally containing gum arabic, talcum, polyvinylpyrrolidone, and/or titanium dioxide, lacquer solutions in aqueous solvents or, for producing coatings resistant to stomach juices, solutions of esters of polyacrylates or polymethacrylates having partially free functional groups, or of suitable cellulose preparations such as acetylcellulose phthalate or hydroxypropyl-methylcellulose phthalate, with or without suitable softeners such as phthalic acid ester or triacetin. Dyestuffs or pigments may be added to the tablets or dragee coatings, for example for identification or marking of the various doses of active ingredient.

One or more withanolide or withanamide preparations which can be administered orally further include hard gelatine capsules, as well as hard or soft closed capsules made from gelatine and, if required, a softener such as glycerin or sorbitol. The hard gelatine capsules can contain one or more of the withanolides in the form of a granulate, for example in admixture with fillers such as maize starch, optionally granulated wheat starch, binders or lubricants such as talcum, magnesium stearate or colloidal silicic acid, and optionally stabilizers. In closed capsules, the one or more of the withanolides is in the form of a powder or granulate; or it is preferably present in the form of a suspension in suitable solvent, whereby for stabilizing the suspensions there can be added, for example, glycerin monostearate.

Other withanolide or withanamide preparations to be administered orally are, for example, aqueous suspensions prepared in the usual manner, which suspensions contain the one or more of the compounds in the suspended form and at a concentration rendering a single dose sufficient. The aqueous suspensions either contain at most small amounts of stabilizers and/or flavoring substances, for example, sweetening agents such as saccharin-sodium, or as syrups contain a certain amount of sugar and/or sorbitol or similar substances. Also suitable are, for example, concentrates or concentrated suspensions for the preparation of shakes. Such concentrates can also be packed in single-dose amounts.

Suitable withanolide or withanamide preparations for rectal administration are, for example, suppositories consisting of a mixture of one or more of the withanolides with a suppository foundation substance. Such substances are, in particular, natural or synthetic triglyceride mixtures. Also suitable are gelatine rectal capsules consisting of a suspension of the one or more of the withanolides or withanamides in a foundation substance. Suitable foundation substances are, for example, liquid triglycerides, of higher or, in particular, medium saturated fatty acids.

Likewise of particular interest are preparations containing the finely ground one or more of the withanolides or withanamides, preferably that having a median of particle size of 5 μm or less, in admixture with a starch, especially with maize starch or wheat starch, also, for example, with potato starch or rice starch. They are produced preferably by means of a brief mixing in a high-speed mixer having a propeller-like, sharp-edged stirring device, for example with a mixing time of between 3 and 10 minutes, and in the case of larger amounts of constituents with cooling if necessary. In this mixing process, the particles of the one or more of the withanolides or withanamides are uniformly deposited, with a continuing reduction of the size of some particles, onto the starch particles. The mixtures mentioned can be processed with the customary, for example, the aforementioned, auxiliaries into the form of solid dosage units; i.e., pressed for example into the form of tablets or dragees or filled into capsules. They can however also be used directly, or after the addition of auxiliaries, for example, pharmaceutically acceptable wetting agents and distributing agents, such as esters of polyoxyethylene sorbitans with higher fatty acids or sodium lauryl sulphate, and/or flavoring substances, as concentrates for the preparation of aqueous suspensions, for example, with about 5- to 20-fold amount of water. Instead of combining the withanolide or withanamide/starch mixture with a surface-active substance or with other auxiliaries, these substances may also be added to the water used to prepare the suspension. The concentrates for producing suspensions, consisting of the one or more of the withanolide or withanamide/starch mixtures and optionally auxiliaries, can be packed in single-dose amounts, if required in an airtight and moisture-proof manner.

In addition, the one or more withanamides or withanolides can be administered to a patient intraperitoneally, intranasally, subcutaneously, or intravenously. In general, for intraperitoneal, intranasal, subcutaneous, or intravenous administration, one or more of the withanolides are provided by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. Preferably, the one or more withanolides are provided in a composition acceptable for intraperitoneal, subcutaneous, or intravenous use in warm-blooded animals or humans. For example, such compositions can comprise a physiologically acceptable solution such as a buffered phosphate salt solution as a carrier for the one or more of the withanamides or withanolides. Preferably, the solution is at a physiological pH. In particular embodiments, the composition is injected directly into the patient perfused through the tumor by intravenous administration.

Preparations according to the present invention comprise one or more of the withanamides or withanolides at a concentration suitable for administration to warm-blooded animals or humans which concentration is, depending on the mode of administration, between about 0.3% and 95%, preferably between about 2.5% and 90%. In the case of suspensions, the concentration is usually not higher than 30%, preferably about 2.5%; and conversely in the case of tablets, dragees and capsules with the one or more of the anthraquinones, the concentration is preferably not lower than about 0.3%, in order to ensure an easy ingestion of the required doses of the one or more withanamides or withanolides. The treatment of patients with the preparations comprising one or more of the withanolides is carried out preferably by one or more administrations of a dose of the one or more withanamide or withanolide which over time is sufficient to substantially inhibit lipid peroxidation. If required, the doses can be administered daily or divided into several partial doses which are administered at intervals of several hours. In particular cases, the preparations can be used in conjunction with or following one or more other therapies such as radiation or chemotherapy. The administered dose of the one or more withanolides or withanamides is dependent both on the patient (species of warm-blooded animal or human) to be treated, the general condition of the patient to be treated, and on the type of disease to be treated.

It is intended that the foregoing description be only illustrative of the present invention and that the present invention be limited only by the hereinafter appended claims.

We claim:

1. An isolated and purified withanamide of the formula:

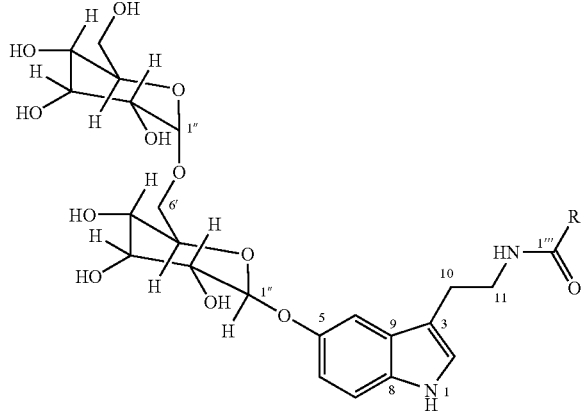

wherein R is selected from the group consisting of:

2. The compound of claim 1 wherein R is (1)

3. The compound of claim 1 wherein R is

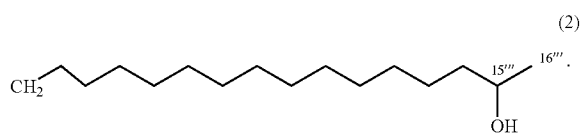
(2)

4. The compound of claim 1 wherein R is

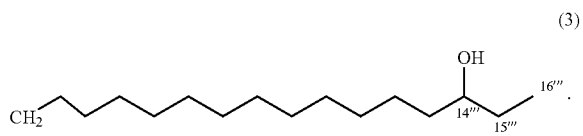
(3)

5. The compound of claim 1 wherein R is

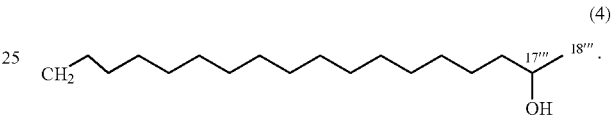
(4)

6. The compound of claim 1 wherein R is

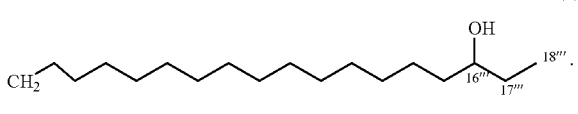
(5)

7. The compound of claim 1 wherein R is

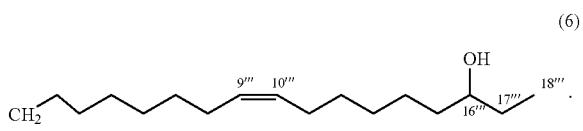
(6)

8. The compound of claim 1 wherein R is

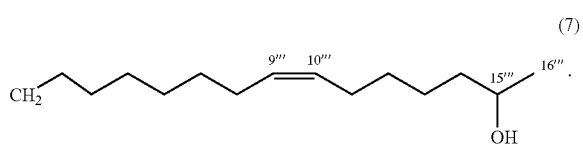
(7)

9. The compound of claim 1 wherein R is

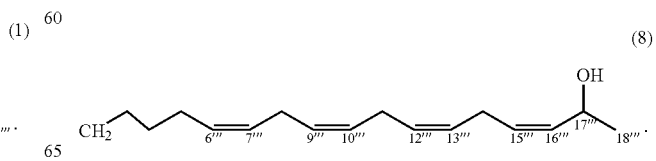
(8)

10. An isolated and purified compound of the formula
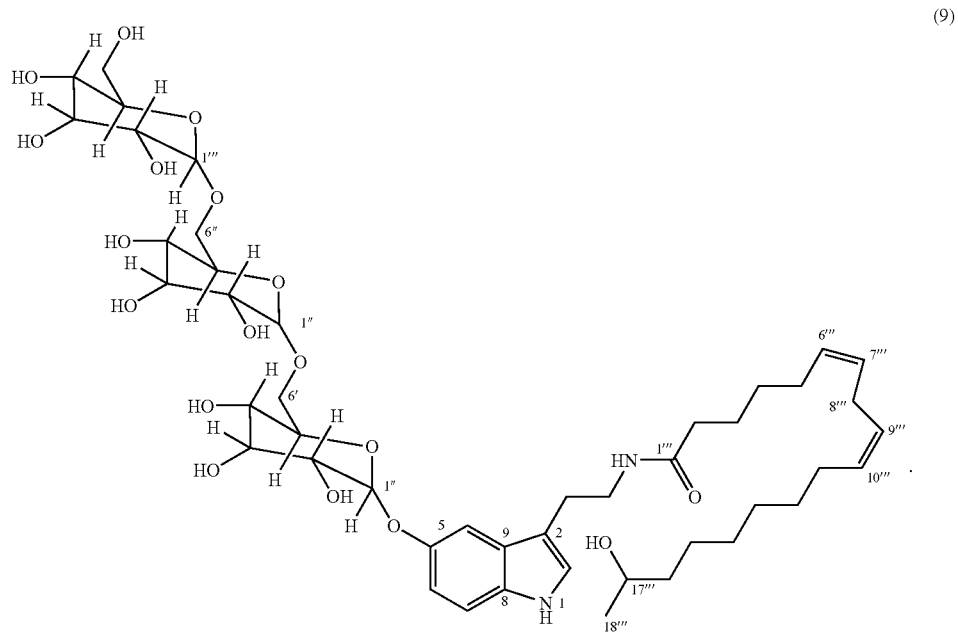
(9)

UNITED STATES PATENT AND TRADEMARK OFFICE
CERTIFICATE OF CORRECTION

| | | |
|---|---|---|
| PATENT NO. | : 7,282,593 B2 | |
| APPLICATION NO. | : 10/918284 | |
| DATED | : October 16, 2007 | |
| INVENTOR(S) | : Muraleedharan G. Nair and Bolleddula Jayaprakasam | |

It is certified that error appears in the above-identified patent and that said Letters Patent is hereby corrected as shown below:

Column 1, line 9, "Application 60,501,985" should be
--Application 60/501,985--.

Column 2, line 9, "(—OH.)" should be --(—OH•)--.

UNITED STATES PATENT AND TRADEMARK OFFICE
CERTIFICATE OF CORRECTION

PATENT NO. : 7,282,593 B2
APPLICATION NO. : 10/918284
DATED : October 16, 2007
INVENTOR(S) : Muraleedharan G. Nair and Bolleddula Jayaprakasam It is certified that error appears in the above-identified patent and that said Letters Patent is hereby corrected as shown below:

Column 23-24, Compound (9),

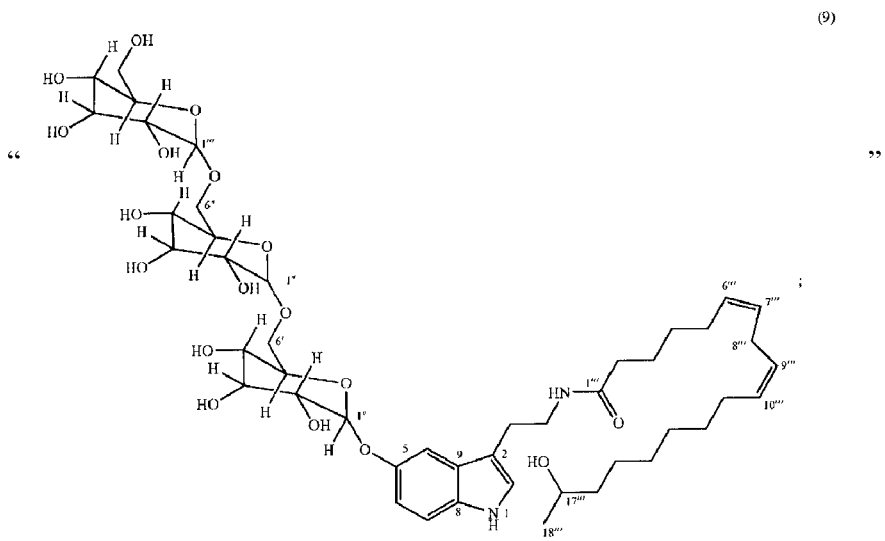

Should be

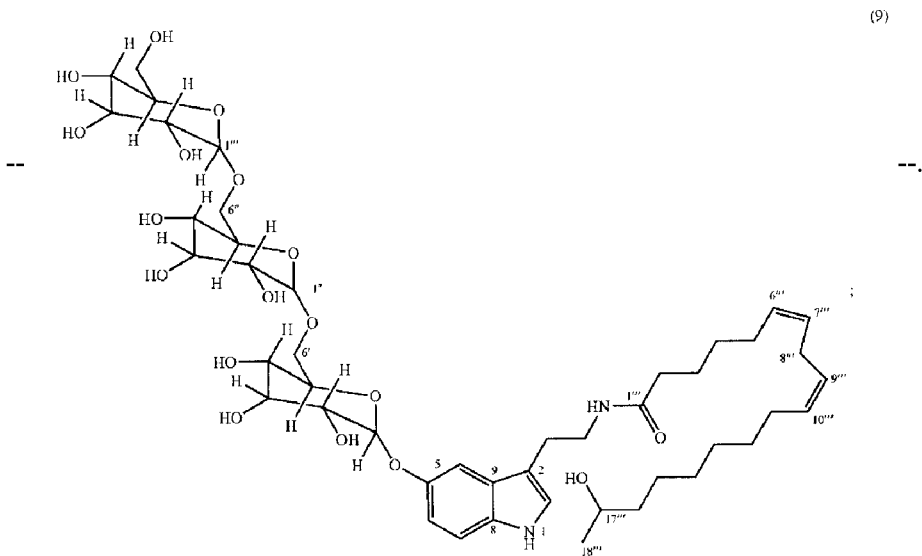

UNITED STATES PATENT AND TRADEMARK OFFICE
CERTIFICATE OF CORRECTION

PATENT NO. : 7,282,593 B2  
APPLICATION NO. : 10/918284  
DATED : October 16, 2007  
INVENTOR(S) : Muraleedharan G. Nair and Bolleddula Jayaprakasam It is certified that error appears in the above-identified patent and that said Letters Patent is hereby corrected as shown below:

Column 28, line 35-50,

"
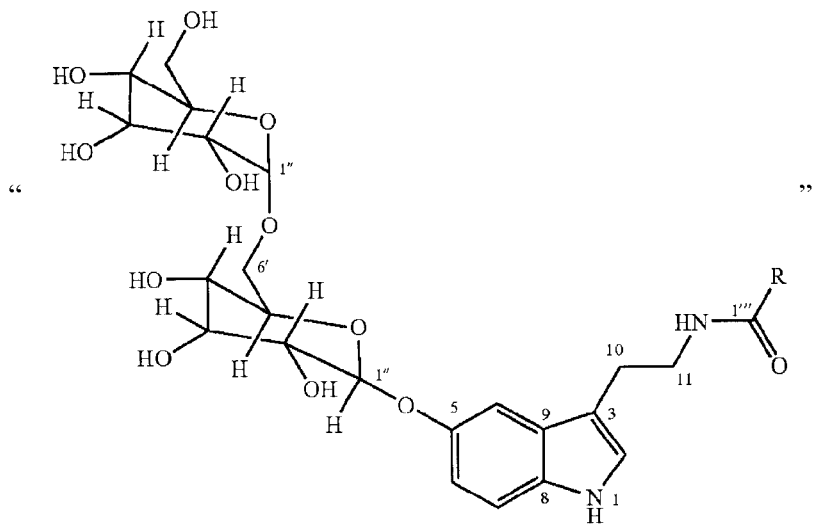
"

Should be

--
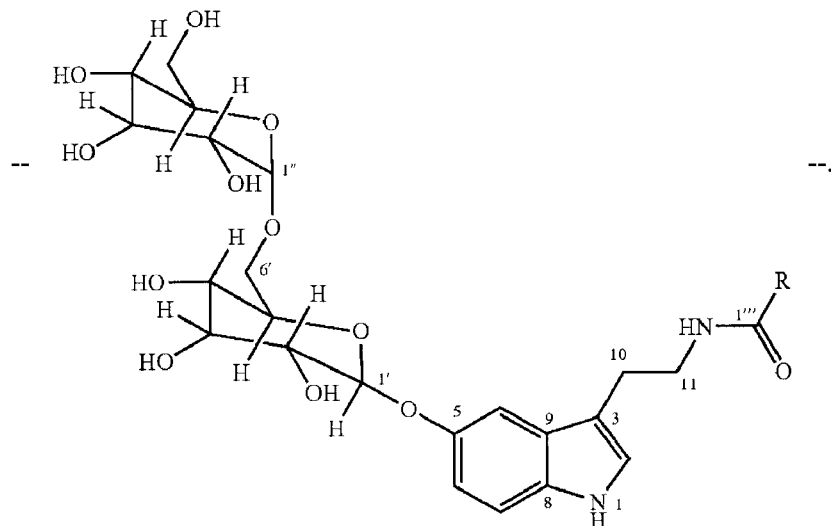
--.

UNITED STATES PATENT AND TRADEMARK OFFICE
CERTIFICATE OF CORRECTION

PATENT NO.        : 7,282,593 B2
APPLICATION NO.   : 10/918284
DATED             : October 16, 2007
INVENTOR(S)       : Muraleedharan G. Nair and Bolleddula Jayaprakasam It is certified that error appears in the above-identified patent and that said Letters Patent is hereby corrected as shown below:

Column 34, line 58, "β-glucopyranoside" should be --β-D-glucopyranoside--.

Column 35, line 10, "DTPT" should be --DEPT--.

Column 36, line 34, "assigned to anometic" should be --assigned to anomeric--.

Column 41, line 16, "1.52(2H, m, H-13″)" should be --1.52(2H, m, H-131‴)--.

Column 41, line 44, "176.3 C-l″)" should be --176.3 (C-1‴)--.

Column 41, line 47, "77.8 (C-17′)" should be --77.8 (C-17‴)--.

Column 42, line 45, "753 [M+H]+" should be --753 [M+H]$^+$--.

Column 42, line 67, "28.2 (C-5′)" should be --28.2 (C-5‴)--.

Column 43, line 20, "(3H, d , J=6.5 Hz, H-6′)" should be --(3H, d, J=6.5 Hz, H-6‴)--.

Column 44, line 6, "hexatrienylph-enylpropionic" should be --hexatrienylphenylpropionic--.

Column 44, line 45, "hydroxyprdpylmethyl" should be --hydroxypropylmethyl--.

UNITED STATES PATENT AND TRADEMARK OFFICE
CERTIFICATE OF CORRECTION

PATENT NO. : 7,282,593 B2
APPLICATION NO. : 10/918284
DATED : October 16, 2007
INVENTOR(S) : Muraleedharan G. Nair and Bolleddula Jayaprakasam It is certified that error appears in the above-identified patent and that said Letters Patent is hereby corrected as shown below:

Column 47, Claim 1,

"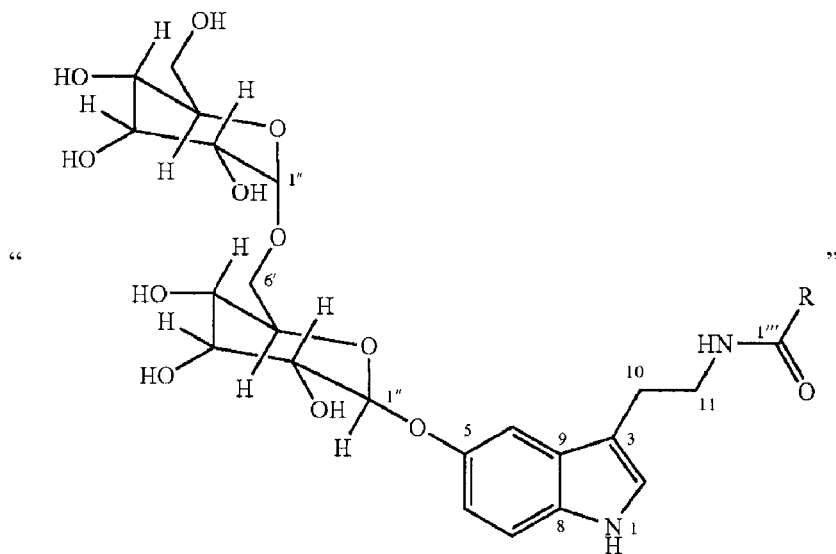"

Should be

--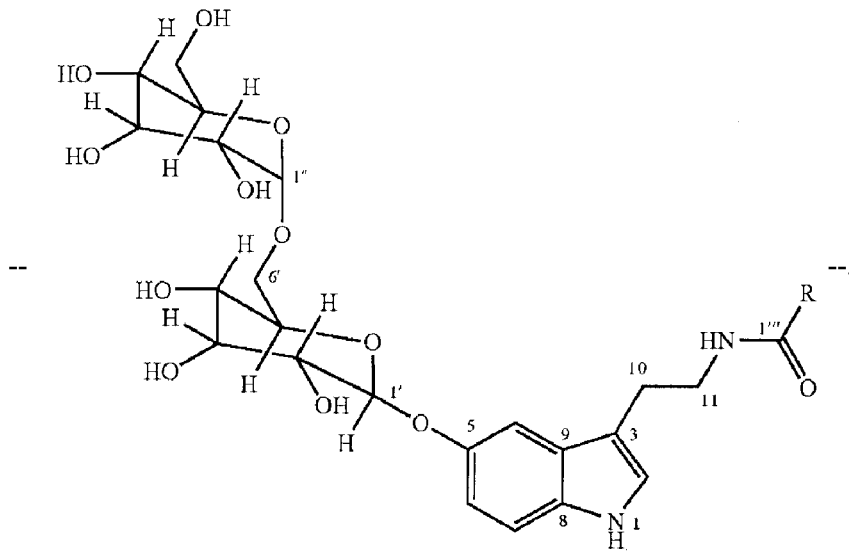--.

UNITED STATES PATENT AND TRADEMARK OFFICE
CERTIFICATE OF CORRECTION

PATENT NO. : 7,282,593 B2
APPLICATION NO. : 10/918284
DATED : October 16, 2007
INVENTOR(S) : Muraleedharan G. Nair and Bolleddula Jayaprakasam It is certified that error appears in the above-identified patent and that said Letters Patent is hereby corrected as shown below:

Column 49-50, Claim 10,

"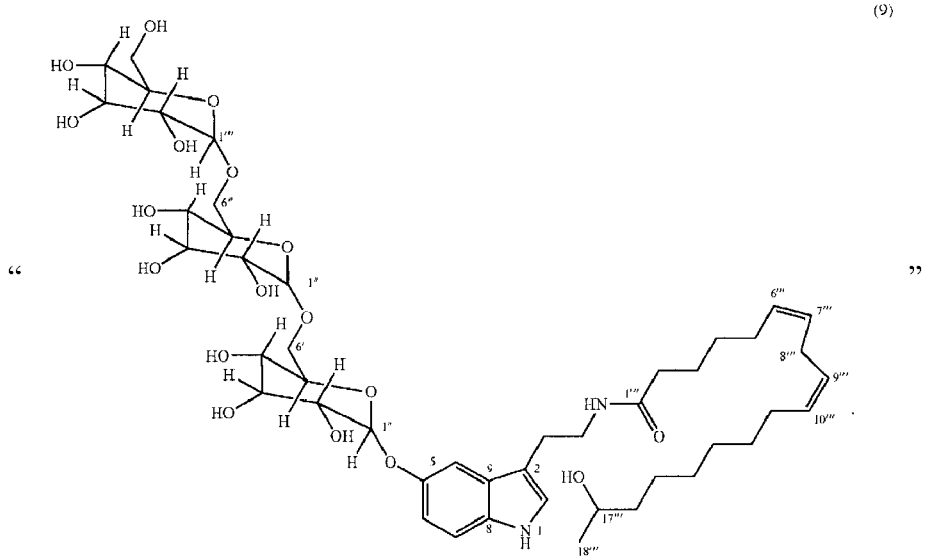"

UNITED STATES PATENT AND TRADEMARK OFFICE
CERTIFICATE OF CORRECTION

PATENT NO. : 7,282,593 B2
APPLICATION NO. : 10/918284
DATED : October 16, 2007
INVENTOR(S) : Muraleedharan G. Nair and Bolleddula Jayaprakasam It is certified that error appears in the above-identified patent and that said Letters Patent is hereby corrected as shown below:

Should be

-- 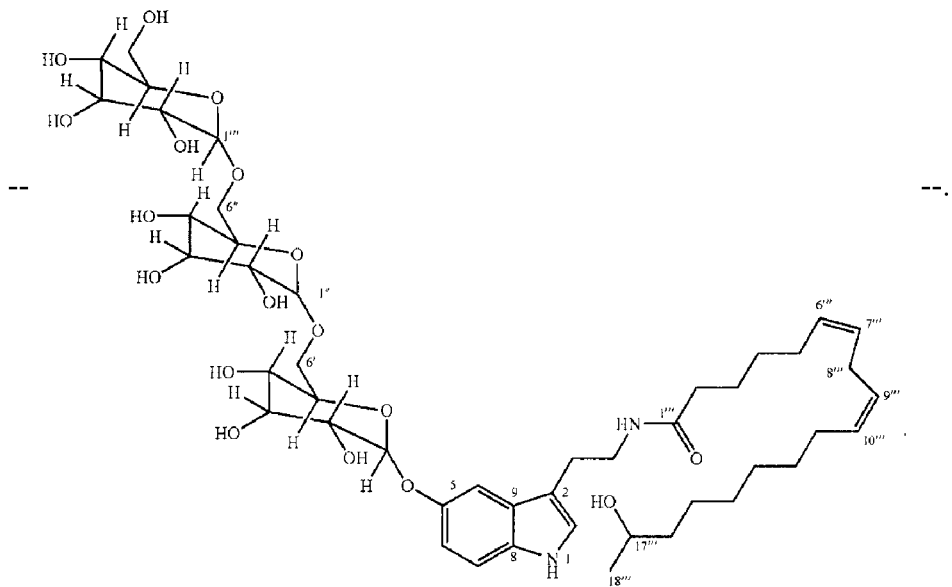 --.

Signed and Sealed this

Fifth Day of May, 2009

JOHN DOLL
*Acting Director of the United States Patent and Trademark Office*

UNITED STATES PATENT AND TRADEMARK OFFICE
CERTIFICATE OF CORRECTION

| | | |
|---|---|---|
| PATENT NO. | : 7,282,593 B2 | |
| APPLICATION NO. | : 10/918284 | |
| DATED | : October 16, 2007 | |
| INVENTOR(S) | : Muraleedharan G. Nair and Bolleddula Jayaprakasam | |

It is certified that error appears in the above-identified patent and that said Letters Patent is hereby corrected as shown below:

Column 1, line 9, "Application 60,501,985" should be --Application 60/501,985--.

Column 2, line 9, "(—OH.)" should be --(—OH•)--.

UNITED STATES PATENT AND TRADEMARK OFFICE
CERTIFICATE OF CORRECTION

PATENT NO. : 7,282,593 B2
APPLICATION NO. : 10/918284
DATED : October 16, 2007
INVENTOR(S) : Muraleedharan G. Nair and Bolleddula Jayaprakasam It is certified that error appears in the above-identified patent and that said Letters Patent is hereby corrected as shown below:

Column 23-24, Compound (9),

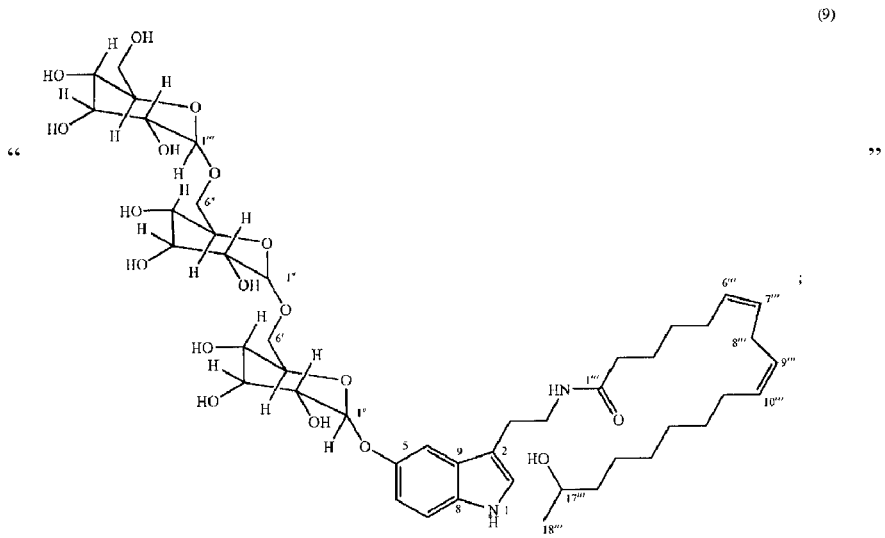

Should be

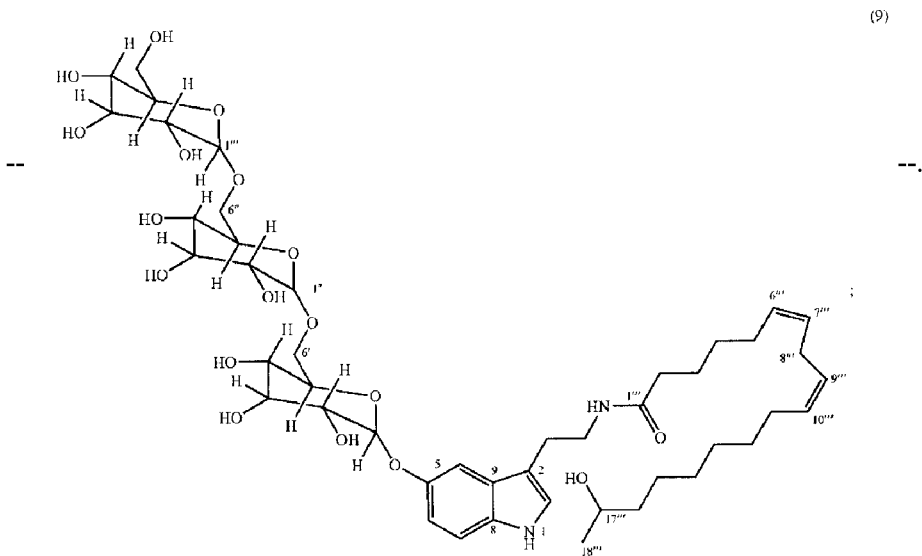

UNITED STATES PATENT AND TRADEMARK OFFICE
CERTIFICATE OF CORRECTION

PATENT NO. : 7,282,593 B2  
APPLICATION NO. : 10/918284  
DATED : October 16, 2007  
INVENTOR(S) : Muraleedharan G. Nair and Bolleddula Jayaprakasam It is certified that error appears in the above-identified patent and that said Letters Patent is hereby corrected as shown below:

Column 28, line 35-50,

"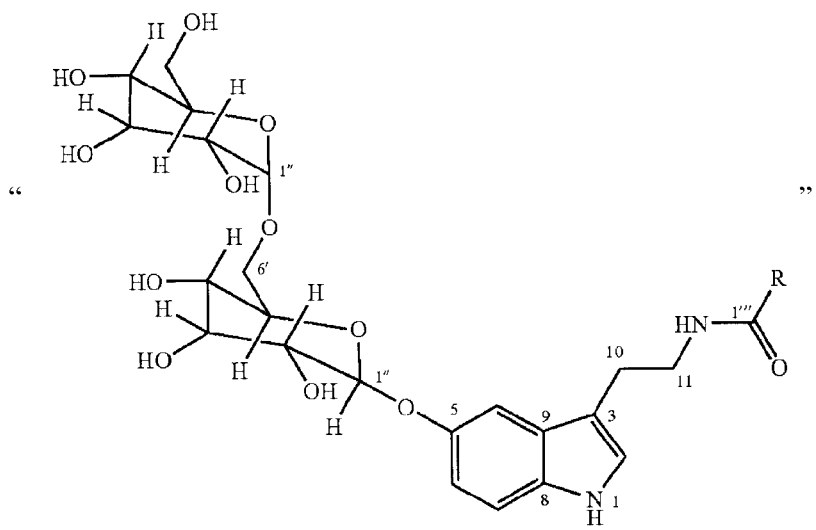"

Should be

--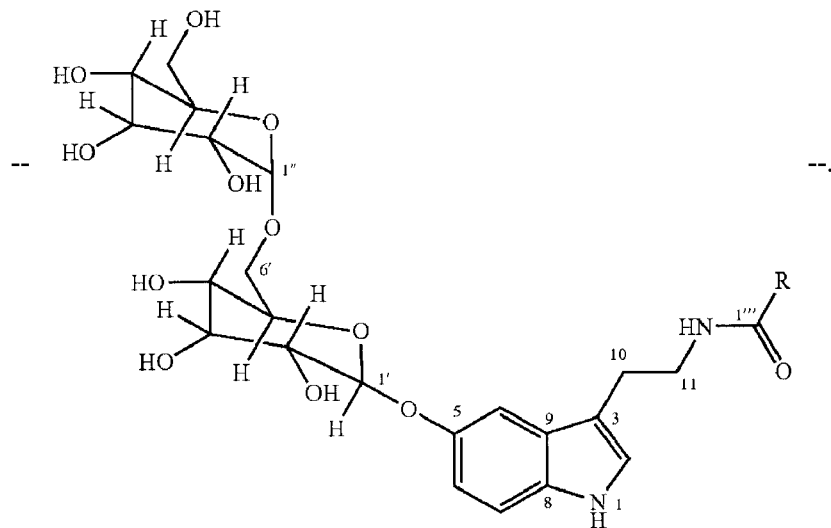--.

UNITED STATES PATENT AND TRADEMARK OFFICE
CERTIFICATE OF CORRECTION

PATENT NO. : 7,282,593 B2
APPLICATION NO. : 10/918284
DATED : October 16, 2007
INVENTOR(S) : Muraleedharan G. Nair and Bolleddula Jayaprakasam It is certified that error appears in the above-identified patent and that said Letters Patent is hereby corrected as shown below:

Column 34, line 58, "β-glucopyranoside" should be --βD-glucopyranoside--.

Column 35, line 10, "DTPT" should be --DEPT--.

Column 36, line 34, "assigned to anometic" should be --assigned to anomeric--.

Column 41, line 16, "1.52(2H, m, H-13")" should be --1.52(2H, m, H-13''')--.

Column 41, line 44, "176.3 C-l')" should be --176.3 (C-1''')--.

Column 41, line 47, "77.8 (C-17')" should be --77.8 (C-17''')--.

Column 42, line 45, "753 [M+H]+" should be --753 $[M+H]^+$--.

Column 42, line 67, "28.2 (C-5')" should be --28.2 (C-5''')--.

Column 43, line 20, "(3H, d , J=6.5 Hz, H-6')" should be --(3H, d, J=6.5 Hz, H-6''')--.

Column 44, line 6, "hexatrienylph-enylpropionic" should be --hexatrienylphenylpropionic--.

Column 44, line 45, "hydroxyprdpylmethyl" should be --hydroxypropylmethyl--.

UNITED STATES PATENT AND TRADEMARK OFFICE
CERTIFICATE OF CORRECTION

PATENT NO. : 7,282,593 B2
APPLICATION NO. : 10/918284
DATED : October 16, 2007
INVENTOR(S) : Muraleedharan G. Nair and Bolleddula Jayaprakasam It is certified that error appears in the above-identified patent and that said Letters Patent is hereby corrected as shown below:

Column 47, Claim 1,

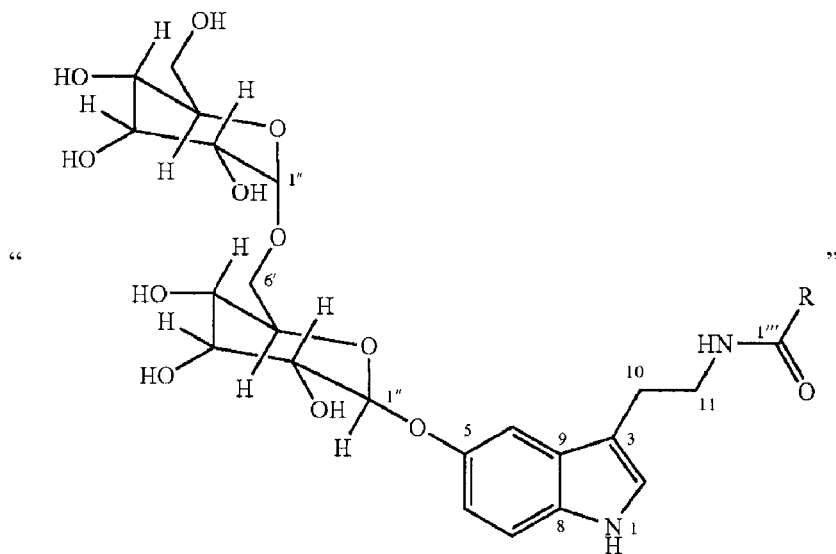

Should be

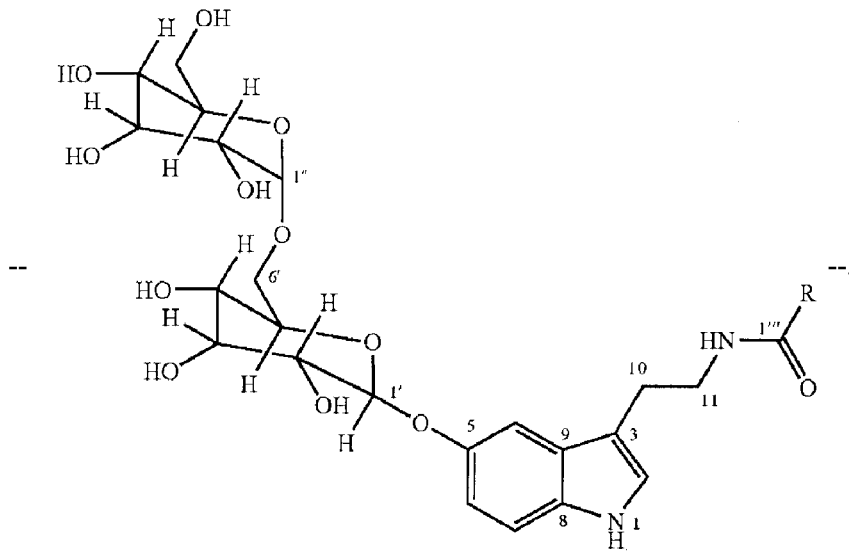

UNITED STATES PATENT AND TRADEMARK OFFICE
CERTIFICATE OF CORRECTION

PATENT NO. : 7,282,593 B2  Page 6 of 7
APPLICATION NO. : 10/918284
DATED : October 16, 2007
INVENTOR(S) : Muraleedharan G. Nair and Bolleddula Jayaprakasam It is certified that error appears in the above-identified patent and that said Letters Patent is hereby corrected as shown below:

Column 49-50, Claim 10,

"  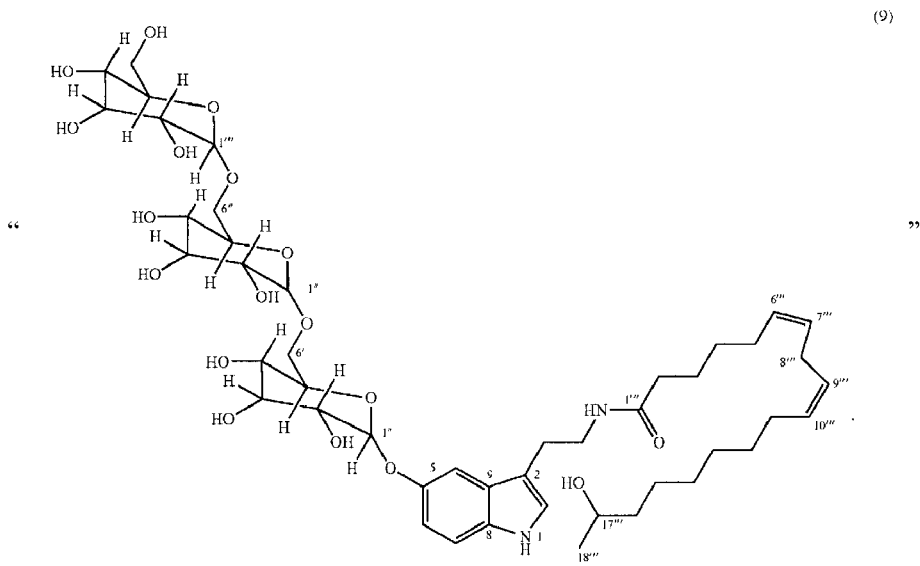  "

UNITED STATES PATENT AND TRADEMARK OFFICE
CERTIFICATE OF CORRECTION

PATENT NO.       : 7,282,593 B2
APPLICATION NO.  : 10/918284
DATED            : October 16, 2007
INVENTOR(S)      : Muraleedharan G. Nair and Bolleddula Jayaprakasam It is certified that error appears in the above-identified patent and that said Letters Patent is hereby corrected as shown below:

Should be

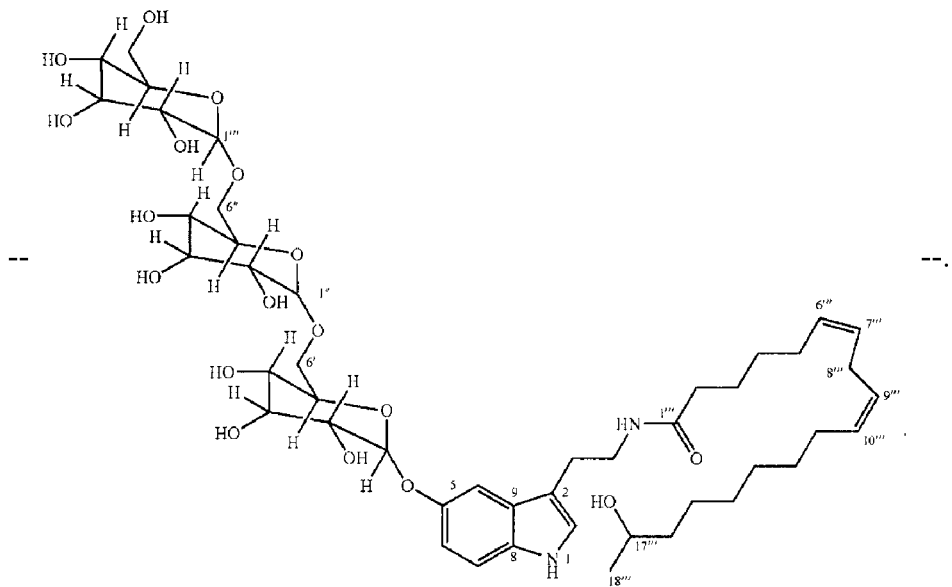

-- --.

This certificate supersedes the Certificate of Correction issued May 5, 2009.

Signed and Sealed this

Thirtieth Day of June, 2009

JOHN DOLL
*Acting Director of the United States Patent and Trademark Office*